(12) United States Patent
Izugami et al.

(10) Patent No.: US 9,707,055 B2
(45) Date of Patent: Jul. 18, 2017

(54) CORRECTION DEVICE

(71) Applicant: Norihiro Izugami, Kobe-shi (JP)

(72) Inventors: Norihiro Izugami, Kobe (JP); Suguru Kondo, Gihu (JP)

(73) Assignee: Norihiro Izugami, Kobe-shi (JP)

( * ) Notice: Subject to any disclaimer, the term of this patent is extended or adjusted under 35 U.S.C. 154(b) by 0 days.

(21) Appl. No.: 15/347,626

(22) Filed: Nov. 9, 2016

(65) Prior Publication Data

US 2017/0049535 A1     Feb. 23, 2017

Related U.S. Application Data

(63) Continuation of application No. 14/635,870, filed on Mar. 2, 2015, now abandoned.

(30) Foreign Application Priority Data

Feb. 28, 2014   (JP) ................................. 2014-039674

(51) Int. Cl.
| | |
|---|---|
| A61C 7/10 | (2006.01) |
| A61C 7/08 | (2006.01) |
| A61C 7/00 | (2006.01) |
| A61C 7/30 | (2006.01) |
| A61C 7/36 | (2006.01) |
| A61C 8/00 | (2006.01) |

(52) U.S. Cl.
CPC ................ *A61C 7/08* (2013.01); *A61C 7/006* (2013.01); *A61C 7/10* (2013.01); *A61C 7/303* (2013.01); *A61C 7/36* (2013.01); *A61C 8/0096* (2013.01)

(58) Field of Classification Search
None
See application file for complete search history.

(56) References Cited

U.S. PATENT DOCUMENTS

| | | | |
|---|---|---|---|
| 5,829,441 A | 11/1998 | Kidd | |
| 8,448,282 B2 | 5/2013 | Stapelbroek | |
| 9,237,940 B2 | 1/2016 | Koklu | |
| 2004/0009449 A1 | 1/2004 | Mah | |
| 2006/0196512 A1 | 9/2006 | Gaskell | |
| 2009/0061375 A1 | 3/2009 | Yamamoto | |

(Continued)

FOREIGN PATENT DOCUMENTS

| | | |
|---|---|---|
| FR | 831155 A | 8/1938 |
| JP | 60-114249 A | 6/1985 |
| JP | 3008730 U | 12/1994 |

(Continued)

*Primary Examiner* — Brian T Gedeon

(74) *Attorney, Agent, or Firm* — Knobbe Martens Olson & Bear LLP

(57) ABSTRACT

An orthodontic appliance can easily achieve and ensure movement of correction target tooth row in a desired direction and achieve highly predictable treatment is provided while anchorage is satisfactorily ensured. A correction device includes a grip member formed to fit to an inner shape of an oral cavity of a patient so as to grip and cover a tooth row, gum parts, and alveolar bone parts of the patient. The correction device includes a first piece 20 covering an area extending from a crown part to a periphery of a cervical part of a correction target tooth and a second piece included in the grip member. The correction device further includes a force applying member 30 provided to connect the first piece 20 to the second piece 10 and configured to move the correction target tooth in a desired direction.

19 Claims, 20 Drawing Sheets

(56) References Cited

U.S. PATENT DOCUMENTS

2009/0142723 A1 6/2009 Govaert
2010/0196837 A1 8/2010 Farrell

FOREIGN PATENT DOCUMENTS

| JP | 2009-279022 A | 12/2009 |
|----|---------------|---------|
| JP | 2009-0297525 A | 12/2009 |
| JP | 2012-223587 A | 11/2012 |
| WO | 01/80762 A2 | 1/2011 |

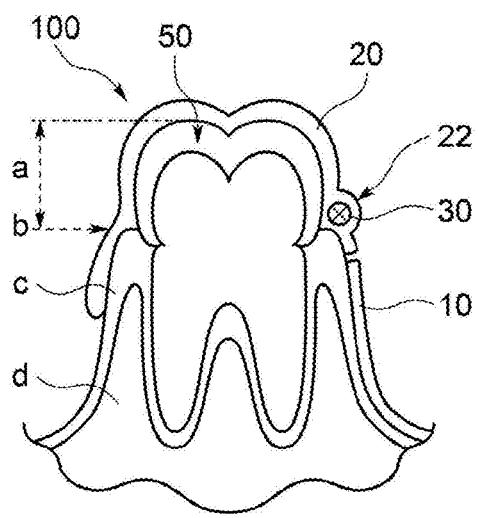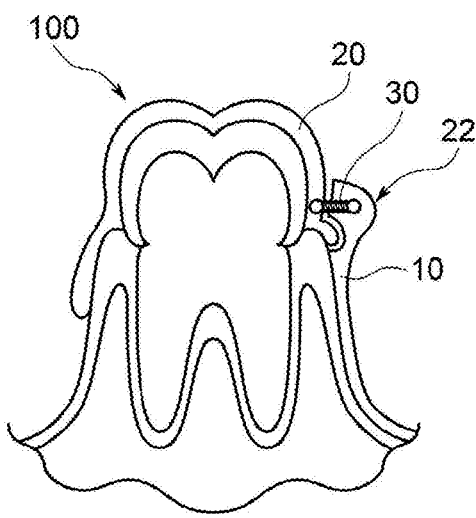
FIG. 2(a)　　　　　　　FIG. 2(b)
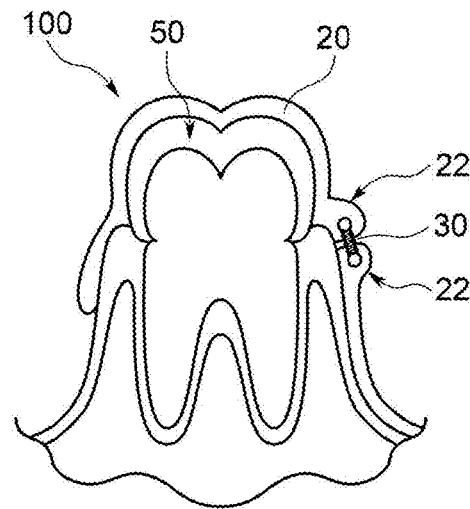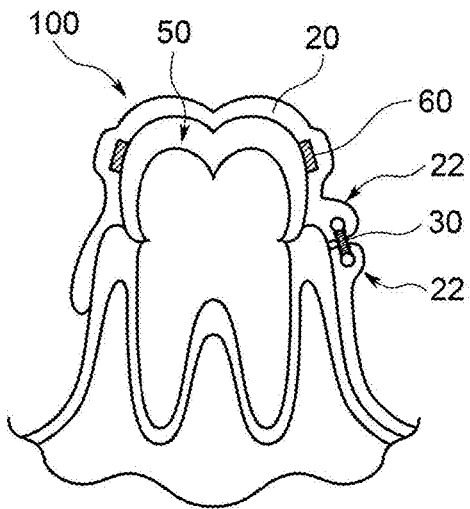
FIG. 2(c)　　　　　　　FIG. 2(d)

BEFORE TREATMENT:
DEVICE IS NOT PLACED

BEFORE TREATMENT:
DEVICE IS PLACED

IN THE COURSE OF TREATMENT:
DEVICE IS PLACED

AFTER TREATMENT:
DEVICE IS NOT PLACED

BEFORE TREATMENT:
DEVICE IS NOT PLACED

BEFORE TREATMENT:
DEVICE IS PLACED

AFTER TREATMENT:
DEVICE IS PLACED

AFTER TREATMENT:
DEVICE IS NOT PLACED

BEFORE TREATMENT:
DEVICE IS NOT PLACED

BEFORE TREATMENT:
DEVICE IS PLACED

AFTER TREATMENT:
DEVICE IS PLACED

AFTER TREATMENT:
DEVICE IS NOT PLACED

CORRECTION DEVICE

CROSS-REFERENCE TO RELATED APPLICATION

This application is a continuation of U.S. application Ser. No. 14/635,870, filed on Mar. 2, 2015, which claims priority to Japanese Patent Application No. 2014-039674, filed Feb. 28, 2014, which are hereby incorporated by reference in their entirety.

TECHNICAL FIELD

The present invention relates to correction devices, and particularly to an orthodontic appliance placed in the oral cavity of a patient to correct tooth alignment of the patient.

BACKGROUND ART

Various orthodontic appliances to correct tooth alignment of patients have been devised. Examples of known fixed-type orthodontic appliances include holding arches and multi-brackets. Examples of known removable-type orthodontic appliances include expansion plates and aligners. On the other hand, in order to correct the entire tooth alignment and to correct bimaxillary protrusion, for example, face masks, headgears, etc. as extraoral anchorage appliances may be used. In recent years, a concept called skeletal anchorage has been introduced, and various experiments have been undertaken to achieve highly predictable orthodontic treatment.

CITATION LIST

Patent Document

[Patent Document 1] Japanese Unexamined Patent Publication No. 2009-279022

[Patent Document 2] Japanese Unexamined Patent Publication No. 2012-223587

SUMMARY OF THE INVENTION

Technical Problem

In the background art, in the case of correction using, for example, a holding arch, a partial tooth row and a partial gum are used as an anchorage, thereby using the force of a wire placed between tooth rows facing each other to move tooth row misalignment of which is to be corrected (correction target tooth row). However, since the holding arch is fixed, a large area contacting with the gum is not possible from the viewpoint of cleanability. The anchorage of the holding arch is weak, and is easily displaced. In the case of the multi-bracket, the returning force of a wire placed on the buccal side or on the lingual side of a tooth row is used to apply certain force to the tooth row, thereby attempting to correct tooth alignment. However, in order to apply desired force only to the correction target tooth row, highly technical and complicated work, e.g., the shape and the installation of a wire, setting the magnitude of the returning force, is required. Therefore, the multi-bracket is not a technique which can be easily used by any orthodontic doctors. In addition, even when the wire is carefully set with prediction, the influence of the reaction force applied to a tooth row adjacent to the correction target tooth row may cause undesirable movement of the adjacent tooth row. The multi-bracket is suitable for movement of a tooth row in buccal-lingual directions, but difficultly moves a tooth row in distal-mesial directions. Since the multi-bracket is fixed, the cleanability of the multi-bracket is not satisfactory.

On the other hand, in the case of the expansion plate as a removable appliance, an expansion screw is provided between divided plates. The screw is turned to move the plates, which cooperate with a wire placed between tooth rows to move a correction target tooth row. However, the expansion plate is partially fixed to teeth by wires. Therefore, small part of the plate is sustained in the oral cavity, so that the plate is easily detached. Moreover, no satisfactory anchorage is provided for the expansion plate. Therefore, the influence of the reaction force is likely to cause unintended movement of a tooth row adjacent to the correction target tooth row. Due to the structure of the expansion plate, the expansion plate only obliquely moves teeth, but difficultly realizes horizontal movement (parallel movement) of teeth. In the case of conventional expansion plate, the expansion screw can only be provided on the lingual side. However, even when the expansion screw cannot be provided on the lingual side due to, for example, a considerably narrow arch, the appliance of the present invention allows the expansion screw to be provided at any place, for example, on the labial side. Therefore, the appliance of the present invention is applicable to remarkably many cases as compared to the conventional types. In the case of an aligner described, for example, in Patent Document 1, a tooth row, gums, and cervical parts are covered along their current shape to ensure a large anchorage. While the large anchorage is ensured, a large force in a desired movement direction which is exerted on a correction target tooth row is obtained, thereby attempting to move the correction target tooth row in the desired movement direction. However, a portion of the aligner corresponding to the correction target tooth row, differently from a portion of the aligner corresponding to other tooth rows, has a shape deviating from the current shape of the correction target tooth row in order to obtain force to move the correction target tooth row in a desired movement direction. It is difficult to place the aligner having such a shape in the oral cavity without deforming portions of the aligner corresponding to the correction target tooth row and a tooth row adjacent to the correction target tooth row. Therefore, only a thin resin having a thickness of about 0.2-0.8 mm can be used as the aligner, so that permanent deformation of the aligner may be easily caused. Thus, the aligner does not fit to the tooth row adjacent to the correction target tooth row, and a gap is formed between the aligner and the tooth row. As a result, at the tooth row adjacent to the correction target tooth row, the anchorage by the aligner does not satisfactorily function, and the tooth row adjacent to the correction target tooth row are greatly influenced by the reaction force of the force applied to the correction target tooth row. Thus, unintended movement of the adjacent tooth row is likely to be caused. The aligner has to be changed a plurality of times in order to correct tooth alignment while accordingly adjusting the distance of movement of the tooth row with the shape of the aligner accordingly stepped up. This increases the period and cost of treatment.

In view of the foregoing, it is an object of the present invention to provide an orthodontic appliance capable of easily achieving and ensuring not only buccal/lingual movement but also distal/mesial movement of a correction target tooth while an anchorage is satisfactorily ensured, so that highly predictable treatment can be achieved in various cases. It is another object of the present invention to provide an orthodontic appliance allowing horizontal movement and inclination of a correction target tooth by satisfactorily ensuring the anchorage. It is another object of the present invention to provide an orthodontic appliance which is easily used together with a skeletal anchor, and has high convenience and excellent aesthetic property.

Solution to the Problem

To achieve the objects, an example of the correction device according to the present invention has the configuration as described below.

That is, a basic configuration of a correction device according to the present invention is a correction device configured to a move correction target tooth of a patient in a desired direction. The correction device includes a grip member formed to fit to an inner shape of the oral cavity of the patient so as to grip and cover a tooth row, and gum parts and alveolar bone parts on the buccal side and the lingual side of the tooth row of the patient. The grip member includes a first piece and a second piece independent of the first piece, and further includes a force applying member provided to connect the first piece to the second piece and configured to move the correction target tooth to the desired direction.

With this basic configuration of the correction device, while at least one of the first piece or the second piece which are independent of each other and included in the grip member is used as a strong anchorage, the correction target tooth gripped by the grip member can be reliably moved in a desired direction by the force applying member. Since at least one of the first piece or the second piece serves as a strong anchorage, teeth gripped as the anchorage is prevented from being moved by a reaction of the force applied to the correction target tooth. The grip member covers an area extending from the crown part to the periphery of the cervical part of a tooth gripped by the grip member. Therefore, the force exerted by the force applying member is applied not only to the crown portion of the correction target tooth but also the entire region to the cervical part. Thus, the horizontal movement but not the inclination movement of the correction target tooth is easily performed. Since the area extending from the crown part to the periphery of the cervical part are covered, gripping force is strong, so that the grip member is less likely to be displaced and detached leading to high efficiency of correction. As described above, with the correction device, it is possible to easily achieve and ensure movement in a desired direction (not only the buccal/lingual movement but also the distal/mesial movement) of the correction target tooth while the anchorage is satisfactorily ensured, so that highly predictable treatment can be achieved.

In the basic configuration of the correction device, when the correction device is used on an upper jaw side, the grip member may further include a palate portion continuous with the portion covering the alveolar bone part on a lingual side of the tooth row and formed to fit to a shape of the palate.

With this configuration, the second piece on the upper jaw side serves as a more stable anchorage via the palate portion.

In a first configuration of the correction device, the first piece grips the correction target tooth to cover an area extending from a crown part to a periphery of a cervical part of a tooth row of the patient, and the second piece covers an area extending from a crown part to a periphery of a cervical part of a tooth row of the patient.

In the first configuration of the correction device, the first piece included in the grip member covers at least an area extending from the crown part to the periphery of the cervical part of a correction target tooth so as to grip the correction target tooth, and the second piece included in the grip member and independent of the first piece covers at least an area extending from the crown part to the periphery of the cervical part of non-target teeth except the correction target tooth. With this configuration, the second piece serves as a strong anchorage. Therefore, by using the force applying member provided to connect the first piece to the second piece, the correction target tooth gripped by the first piece can be moved in a desired direction. At this time, since the second piece serves as a strong anchorage, the non-target teeth gripped by the second piece are prevented from being moved by reaction force of the force applied to the correction target tooth gripped by the first piece. Since the second piece serves as a strong anchorage, using the force applying member allows the movement of the correction target tooth not only in a desired direction, i.e., in the buccal-lingual direction but also in a distal direction and a mesial direction which are conventionally difficult directions and also in upward and downward directions. Moreover, the first piece covers at least an area extending from the crown part to the periphery of the cervical part of the correction target tooth. Therefore, the force by the force applying member is applied not only to the crown portion of the correction target tooth but also the entire region to the cervical part. Thus, the horizontal movement but not the inclination movement of the correction target tooth is easily performed. The correction target tooth is not moved by using the property of the grip member itself while the anchorage is ensured. While the anchorage is ensured, the force applying member which is independent of the grip member including the first piece and the second piece moves the correction target tooth. Therefore, it is possible to ensure the movement of the correction target tooth in a desired direction. As described above, with the correction device according to the present invention, it is possible to easily achieve and ensure not only the buccal/lingual movement but also the distal/mesial movement of the correction target tooth while the anchorage is satisfactorily ensured, so that highly predictable treatment can be achieved.

The correction device covers the entire teeth and the large portion of the gum, so that the force applying member can be provided at any position of the correction device. Thus, the correction device is applicable to many cases. Even when the correction device is changed due to step up, a post-aligned tooth is used together with the existing anchorage so as to be a new anchorage, so that it is possible to set a new second piece serving as a more stable anchorage. With this configuration, the new second piece can also serve as a retainer to prevent the post-aligned tooth from returning to its pre-alignment position.

In the correction device of the first configuration, a skeletal anchor may be implanted in the second piece.

Thus, a skeletal anchor such as a mini screw or an implant which serves as a definitive anchorage is implanted in the second piece, so that the second piece serves as a stable and definitive anchorage. This is very effective, in particular, when the entire tooth row including the alveolar bone of a patient is moved in the front, rear, left, and right directions, for example, in the buccal-lingual directions and in the distal-mesial directions with respect to the cranial bone and the jawbone. Cases subjected to surgical orthodontics such as osteotomy involving high risks can be reduced as much as possible. In setback movement of the entire tooth row by a currently trialed method in which a multi-bracket is used together with a skeletal anchor, force is obliquely exerted, so that three dimensional misalignment may be caused, and forward and lateral movement is currently impossible. However, in the present correction device, no three dimensional misalignment is caused, and the forward and lateral movement is also possible.

In a second configuration of the correction device, the first piece may grip the correction target tooth to cover an area extending from a crown part to a periphery of a cervical part of a tooth row of a patient, the second piece may grip a correction target tooth, which is different from the correction target tooth gripped by the first piece, to cover an area extending from a crown part to a periphery of a cervical part of a tooth row of the patient, and when the correction device is used for a lower jaw, the first piece and the second piece may extend to positions close to front teeth, and the force applying member may be positioned near the front teeth.

In the second configuration of the correction device, both of the first piece and the second piece of the grip member cover at least an area extending from the crown part to the periphery of the cervical part of a correction target tooth to grip the correction target tooth. With this configuration, while the first piece and the second piece serve as a strong anchorage, the force applying member provided to connect the first piece to the first piece can be used to move the correction target tooth gripped by the first piece and the second piece in a desired direction. Similarly to the first configuration, the first piece and the second piece serve as a strong anchorage also in the second configuration. This prevents movement caused by reaction force of the force applied to the gripped correction target tooth. Similarly to the first configuration, not only movement in the buccal-lingual directions, but also movement in the distal direction and the mesial direction, and also the upward and downward directions which are conventionally difficult directions are possible. Moreover, the horizontal movement but not the inclination movement of the correction target tooth is easily performed. Movement of the correction tooth in a desired direction by using the force applying member can be ensured. In particular, this configuration is more suitable when a correction target tooth gripped by the first piece and a correction target tooth gripped by the second piece are in a symmetric positional relationship.

In a third configuration of the correction device, the first piece grips the correction target tooth to cover an area extending from a crown part to a periphery of a cervical part of a tooth row of a patient, the second piece grips a correction target tooth, which is different from the correction target tooth gripped by the first piece, to cover an area extending from a crown part to a periphery of a cervical part of a tooth row of the patient, and when the correction device is used for an upper jaw, the force applying member is provided on the palate portion.

With the third configuration of the correction device, advantages similar to those obtained by the second configuration used for the lower jaw can be obtained. Similarly, the third configuration is more suitable when a correction target tooth gripped by the first piece and a correction target tooth gripped by the second piece are in a symmetric positional relationship.

The third configuration of the correction device may further include a third piece forming the grip member, formed independently of and near the first piece and the second piece, and covering an area extending from the crown part to the periphery of the cervical part of a tooth row of the patient, and a fixing member connected to the force applying member and extending from the force applying member to the third piece.

With this configuration, the third piece serves as a strong anchorage. Thus, using the strong anchorage, it is possible to more reliably move the correction target teeth gripped by the first piece and the second piece in a desired direction. In a fourth configuration of the correction device, the first piece may grip the correction target tooth to cover an area extending from the crown part to the periphery of the cervical part of a tooth row of the patient, and a skeletal anchor may be implanted in the second piece.

Thus, a skeletal anchor such as a mini screw or an implant which serves as a definitive anchorage is implanted in the second piece, so that the second piece serves as a strong and definitive anchorage. This is very effective, in particular, when the entire tooth row including the alveolar bone of a patient is moved in the front, rear, left, and right directions, for example, in the buccal-lingual directions and in the distal-mesial directions with respect to the cranial bone and the jawbone. Cases subjected surgical orthodontics such as osteotomy involving high risks can be reduced as much as possible. In setback movement of the entire tooth row by a currently trialed method in which a multi-bracket is used together with a skeletal anchor, force is obliquely exerted, so that three dimensional misalignment may be caused, and forward and lateral movement is currently impossible. However, in the present correction device, no three dimensional misalignment is caused, and the forward and lateral movement is also possible.

In the correction device according to the present invention, the desired direction is a distal or mesial direction, a lingual side or buccal side direction, or an upward or downward direction with respect to the tooth row.

In the correction device according to the present invention, when there is a correction target tooth to be obliquely moved in the lingual side or buccal side direction, a portion of the grip member covering the crown part of the correction target tooth to be obliquely moved is preferably removed on the buccal side or the lingual side.

As described above, the portion of the grip member covering the crown part of the correction target tooth to be obliquely moved has been partially removed on the buccal side or on the lingual side. Therefore, force applied by the force applying member is not received by the entire region from the crown portion to the cervical part, but the force is applied in an oblique direction so that the tooth is inclined toward the side where the portion of the grip member at the crown has been removed. Thus, it is also possible to obliquely move the correction target tooth.

In the correction device according to the present invention, a wire, a screw, a spring, an orthodontic rubber, or a magnet may be used as the force applying member.

In the correction device according to the present invention, the screw, the spring, the orthodontic rubber, or the magnet may be provided to extend over the first piece and the second piece in a direction corresponding to the moving direction.

In this case, the first piece and the second piece each has a portion into which a screw, spring, orthodontic rubber, or a magnet is incorporated, and the portion is formed as a thick part.

In the correction device according to the present invention, it is aesthetically advantageous when the grip member is made of a transparent resin.

In the correction device according to the present invention, the grip member preferably has a portion having a two-layer structure. The portion having the two-layer structure includes a lower layer which is a membrane sheet made of silicon and an upper layer made of the transparent resin.

With this configuration, the grip member can be used together with, for example, a fixed-type multi-bracket. That is, when a wire is placed on the entire tooth row by a button, the correction target tooth can be moved as described above by the correction device with the multi-bracket covered with the silicon membrane sheet which is the lower layer. As described above, the correction device can also be used as a rescue system of the multi-bracket. That is, orthodontic treatment providing a synergistic effect obtained by combining the advantage obtained by the multi-bracket with the advantage obtained by the correction device is also possible. The structure is effective in the case of crowding in the oral cavity of a patient similarly to the case where a multi-bracket is used.

In the correction device according to the present invention, the transparent resin may contain carbon.

With this configuration, the gripping force of the grip member can be enhanced, so that a more stable anchorage is ensured, and movement of the correction target tooth in a desired direction can be further ensured. When the grip member made of a transparent resin is used as an aligner, carbon is partially used such that a portion which is preferably flexible and a portion which is preferably non-flexible are formed to have the same resin thickness. In this way, it is also possible to handle movement of a long tooth row depending on the condition of the tooth row of a patient.

In the correction device according to the present invention, the grip member may cover a region including the tooth row, the gum parts, and highest contour portions of the alveolar bone part on the buccal side of the tooth row.

In the correction device according to the present invention, the grip member may be configured to grip the entire tooth row of a patient.

With this configuration, all the teeth of a patient gripped by the grip member can be moved in a desired direction by using the force applying member. That is, the entire tooth row inclusive of the alveolar bone parts of the patient can be moved in a desired directions to the front, rear, left, and right (e.g., buccal-lingual directions, distal-mesial directions) with respect to the cranial bone and the jawbone. Therefore, bimaxillary protrusion, bimaxillary overgrowth and underdevelopment can be treated, so that physical and aesthetic stress caused when conventional facial masks or headgears are used can be significantly reduced. In particular, in a conventional method, i.e., a facial mask or a headgear for moving the entire tooth row, the entire tooth row can be moved in front and rear directions, but a tooth row displaced in the left or right direction due to behavior, etc. cannot be moved to the right or left direction. The present correction device allows movement in right-left directions which is conventionally difficult. Moreover, in the case of severe bimaxillary overgrowth/underdevelopment, the grip member can be pulled or pushed in combination with an extraoral anchorage such as the facial mask and the headgear or an intramaxillary anchorage, so that application of stronger force to move the entire tooth row is possible.

In the correction device according to the present invention, the first piece may be used for the upper jaw, and covers an area extending from the crown part to the periphery of the cervical part of the entire tooth row of the upper jaw of the patient, the second piece may be used for the lower jaw, and covers an area extending from the crown part to the periphery of the cervical part of the entire tooth row of the lower jaw of the patient, and the force applying member may be an intermaxillary rubber.

According to a fifth configuration of the correction device, when a patient has an overgrown or underdeveloped upper jaw and an overgrown or underdeveloped lower jaw, and the tooth row of the upper jaw and the tooth row of the lower jaw are displaced with respect to each other, the displacement can be corrected by using, for example, the intermaxillary rubber as a force applying member disposed at the first piece covering an area extending from the crown part to the periphery of the cervical part of the entire tooth row of the upper jaw and the second piece covering a region from the crown part to a periphery of the cervical part of the entire tooth row of the lower jaw. In particular, when the upper jaw is overgrown, and the lower jaw is underdeveloped, or when the upper jaw is underdeveloped, and the lower jaw is overgrown, the displacement between the lower jaw and the upper jaw can be effectively corrected without using a skeletal anchor.

A skeletal anchor may be implanted in both or one of the first piece and the second piece.

For example, when a skeletal anchor is implanted in a piece for the upper jaw, and no skeletal anchor is implanted in a piece for the lower jaw, the upper jaw serves as an anchorage, and a tooth row of the lower jaw can be primarily moved in an intended direction depending on the direction in which the intermaxillary rubber is attached. In contrast, when no skeletal anchor is implanted in a piece for the upper jaw, and a skeletal anchor is implanted in a piece for the lower jaw, the lower jaw serves as an anchorage, and a tooth row of the upper jaw can be moved. When a skeletal anchor is implanted in a piece for each of the upper jaw and the lower jaw, the intermaxillary rubber serves as a member applying opposite forces. Thus, growth promotion/growth inhibition of the entire the jawbone and the facial bone including the entire tooth row fixed by the skeletal anchor is possible. Depending on the direction in which the intermaxillary rubber is attached, growth promotion/growth inhibition of the upper jawbone and the face bone around the upper jaw bone or growth promotion/growth inhibition of the lower jawbone and the face bone around the lower jaw bone is possible.

Advantages of the Invention

With the correction device according to the present invention, it is possible to easily achieve and ensure not only the buccal/lingual movement but also the distal/mesial movement of the correction target tooth while the anchorage is satisfactorily ensured, so that highly predictable treatment can be achieved.

BRIEF DESCRIPTION OF THE DRAWINGS

FIGS. 1(a) and 1(b) are views illustrating an example structure of a correction device according to an embodiment of the present invention, wherein FIG. 1(a) shows a correction device used on a lower jaw side, and FIG. 1(b) shows a correction device used on an upper jaw side.

FIGS. 2(a)-2(d) are cross sectional views illustrating various example structures of the correction device according to the embodiment of the present invention placed on a tooth row.

FIG. 6(a) shows a correction device used on the lower jaw side, and FIG. 6(b) shows a correction device used on the upper jaw side.

FIG. 8(a) shows a correction device used on the lower jaw side, and FIG. 8(b) shows a correction device used on the upper jaw side.

FIG. 9(a) shows a correction device for on the lower jaw side, and FIG. 9(b) shows a correction device used on the upper jaw side.

FIG. 10(a) shows a correction device used on the lower jaw side, and FIG. 10(b) shows a correction device used on the upper jaw side.

FIG. 11(a) shows a correction device used on the lower jaw side, FIG. 11(b) shows a correction device used on the upper jaw side, and FIG. 11(c) shows a correction device in which fixing members drawn out of the force applying member are provided at grip members near the first piece and the second piece.

FIGS. 12(a) and 12(b) are photos showing examples of correction devices according to an embodiment of the present invention, wherein FIG. 12(a) shows an example in which a row of two teeth from the back is moved by a correction device used on the upper jaw, and FIG. 12(b) shows an example in which the correction device used on the upper jaw side is divided at the center thereof so that a first piece and a second piece of a grip member are formed to have the same size, so that opposite forces are applied to tooth rows facing each other by the force applying member, and tooth rows on the left and on the right are moved together by the same distance. In this case, a conventional expansion plate causes oblique movement, but the present invention allows horizontal movement (parallel movement). At the same time, the present invention also allows compression of left and right tooth rows which was difficultly realized by removable-type appliances. The present invention also allows horizontal movement.

FIG. 13(a) shows an example in which lower jaw underdevelopment or upper jaw overgrowth is corrected without using a skeletal anchor, FIG. 13(b) shows an example in which a skeletal anchor is implanted in a grip member on the upper jaw side to correct the lower jaw overgrowth, and FIG. 13(c) shows an example in which a skeletal anchor is implanted in the grip members on the upper jaw side and the lower jaw side to correct the lower jaw overgrowth or the upper jaw underdevelopment.

DESCRIPTION OF EMBODIMENTS

An embodiment of the present invention will be described below with reference to the drawings.

Figure 1A:
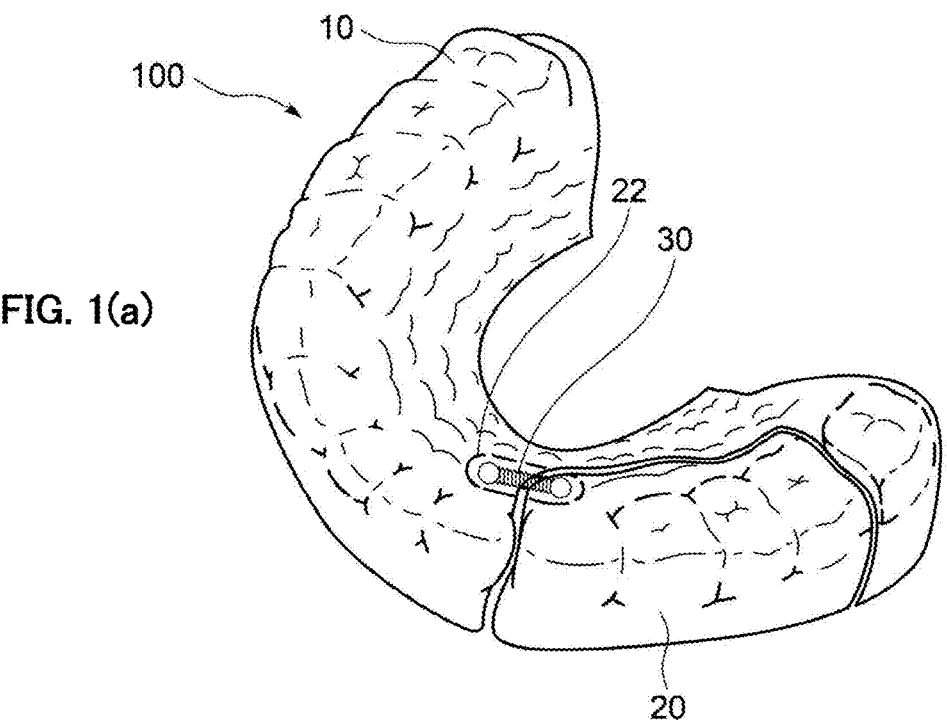
Figure 1B:
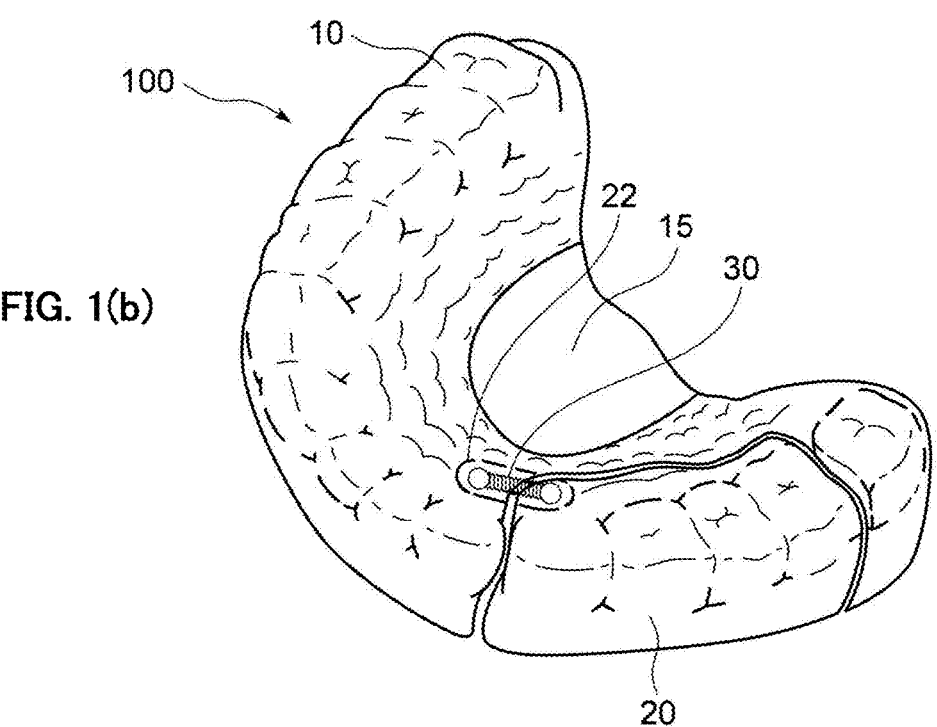

FIGS. 1(a) and 1(b) are views illustrating an example structure of a correction device according to an embodiment of the present invention, wherein FIG. 1(a) shows a correction device used on a lower jaw side, and FIG. 1(b) shows a correction device used on an upper jaw side.

As illustrated in FIG. 1(a), a correction device 100 according to the present embodiment includes a grip member which is configured to be used both on the upper jaw side and on the lower jaw side, is made of, for example, a resin material to fit to an inner shape of the oral cavity of a patient so as to grip and cover a tooth row, gum parts, and alveolar bone parts of the patient, and includes a first piece 20 and a second piece 10. Specifically, the grip member covers a tooth row, and gum parts and alveolar bone parts on a buccal side and a lingual side of the tooth row. The first piece 20 included in the grip member covers at least an area extending from the crown part to the periphery of the cervical part of a tooth misalignment of which is to be corrected (correction target tooth) so as to grip the correction target tooth. The second piece 10 included in the grip member is part of the grip member except the first piece 20 and is formed as a piece independent of the first piece 20. A force applying member 30 is provided to connect the first piece 20 to the second piece 10. The force applying member 30 moves the correction target tooth in a desired direction. Here, for example, a wire, a screw, a spring, a rubber, or a magnet can be used as the force applying member 30. FIG. 1(a) illustrates an example in which a gap is formed between a back tooth located at an innermost position in the oral cavity and a tooth adjacent to the back tooth, and a tooth row covered with the first piece 20 is moved in a direction toward the back tooth by using, for example, an expansion or contraction screw as the force applying member 30, wherein the screw is placed on the first piece 20 and the second piece 30 to extend over the first piece 20 and the second piece 10. In this example, expanding the screw allows the tooth row covered with the first piece 20 to move in a direction toward the back tooth. Portions of the first piece 20 and the second piece 10 on which the force applying member 30 is provided have an increased thickness by the force applying member 30, and the portions having the increased thickness are thick portions 22(see, for example, FIG. 2).

As illustrated in FIG. 1(b), when the correction device 100 according to the present embodiment is used on the upper jaw side, the second piece 10 preferably further includes a palate portion 15 continuous with a portion covering the alveolar bone part located on the lingual side of the tooth row and formed to fit to the shape of the palate. Note that the example in which a tooth row covered with the first piece 20 is moved is similar to that described with reference to FIG. 1(a).

Next, FIGS. 2(a)-2(d) are cross-sectional views illustrating various example structures of the correction device 100 according to the embodiment of the present invention, wherein in the cross-sectional view, the first pieces 20 of FIG. 1(b) are taken along a direction from the buccal side to the lingual side of the tooth row, and a portion including the force applying member 30 connecting the first piece 20 to the second piece 10 is shown.

As illustrated in FIG. 2(a), the first piece 20 covers a tooth row including a correction target tooth 50 and a region at least an area extending from a crown part a on both of the buccal side (on the left in the plane of the paper) and the lingual side (on the right in the plane of the paper) of the tooth row to a peripheral portion of the cervical part b to fit to the shapes of the crown part a and the peripheral portion of the cervical part b. The second piece 10 covers a tooth row of non-target teeth (not shown) and at least an area extending from a crown part a on both of the buccal side (on the left in the plane of the paper) and the lingual side (on the right in the plane of the paper) to the cervical part b of the tooth row. At the portion of the correction target tooth 50 in FIG. 2(a), the second piece 10 covers at least an area extending from the periphery of the cervical part b on the lingual side of the tooth row of the correction target tooth 50 to the alveolar bone part d. FIG. 2(a) shows the correction device used on the upper jaw side, and thus the second piece 10 continuously covers the palate portion. The first piece 20 may also cover a relatively large area from a gum part c to an alveolar bone part d on the buccal side (on the left in the plane of the paper) of the correction target tooth 50 (see for example, FIG. 10). In order to connect the first piece 20 to the second piece 10, the force applying member 30 is provided along a direction in which the teeth are aligned (i.e., distal direction or mesial direction) in FIG. 2(a). Thus, expansion or contraction of, for example, the screw as the force applying member 30 is caused to move the correction target tooth 50 gripped by the first piece 20 in the distal direction or the mesial direction (in a direction perpendicular to the plane of the paper or in a direction away from the plane of the paper).

FIG. 2(b) shows an example in which the force applying member 30 is provided at a position different from the position shown in FIG. 2(a). The force applying member 30 is provided on a lingual side portion of the correction target tooth 50 in a lingual side-buccal side direction of the tooth row. Thus, expansion or contraction of, for example, the screw as the force applying member 30 is caused to move the correction target tooth 50 gripped by the first piece 20 in a buccal side direction or a lingual side direction.

FIG. 2(c) shows an example in which the force applying member 30 is provided at a position different from the positions shown in FIGS. 2(a) and 2(b). The force applying member 30 is provided on the lingual side portion of the correction target tooth 50 in a lower side-upper side direction (a direction from the lower jaw toward the upper jaw) of the tooth row. Thus, expansion or contraction of, for example, the screw as the force applying member 30 is caused to move the correction target tooth 50 gripped by the first piece 20 in the upper side direction or in the lower side direction. As described above, when for example, a screw, a spring, an orthodontic rubber, or a magnet is used, the force applying member 30 is provided to extend over the first piece 20 and the second piece 10 in a direction corresponding to an intended moving direction, so that it is possible to move the correction target tooth 50 in the direction in which the force applying member 30 is provided.

As illustrated in FIG. 2(d), projecting members 60 such as square buttons are provided to the configuration of FIG. 2(c) on the buccal side portion and the lingual side portion of the crown part a. This configuration ensures that the first piece 20 covering the correction target tooth 50 is not detached when the correction target tooth 50 is moved in the upper side direction.

Figure 3:
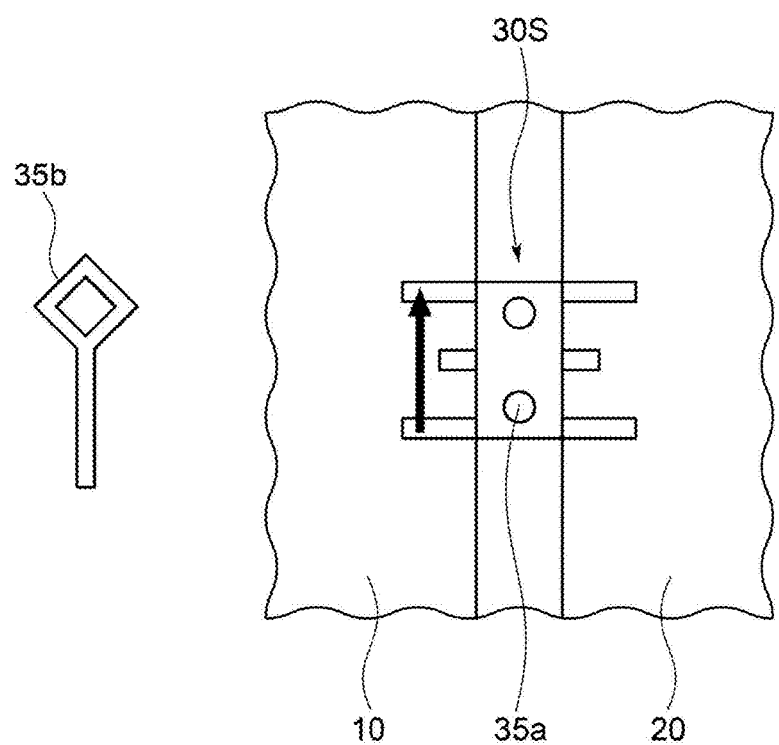
FIG. 3 is a view illustrating an example of a force applying member of the correction device according to the embodiment of the present invention.

Here, the force applying member 30 may be, as described above, for example, a screw, a spring, an orthodontic rubber, or a magnet, wherein a screw 30S illustrated in FIG. 3 can be used as an example of the screw. As illustrated in FIG. 3, the screw 30S is disposed to connect the first piece 20 to the second piece 10. A pin 35b is inserted into a hole 35a formed at the center of the screw 30S, and the pin 35b is turned in a direction indicated by the arrow or in a direction opposite to the arrow, thereby the first piece 20 and the second piece 10 are moved to be away from each other or to be close to each other. In this way, for example, a correction target tooth gripped by the first piece 20 (note that the second piece 10 may grip a correction target tooth as described later) can be moved in a desired direction. The screw illustrated in FIG. 3 is a general screw similar to a screw generally used for an expansion plate.

Next, FIGS. 4(a) and 4(b) and FIGS. 5(a) and 5(b) sequentially illustrate example steps in a method of manufacturing the correction device according to the present embodiment.

Figure 4A:
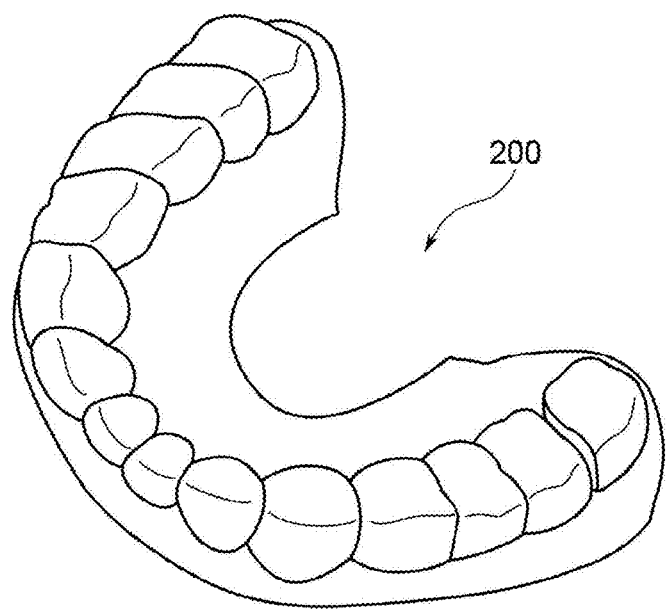
FIGS. 4(a) and 4(b) are views illustrating steps in a method of manufacturing the correction device according to the embodiment of the present invention.
Figure 4B:
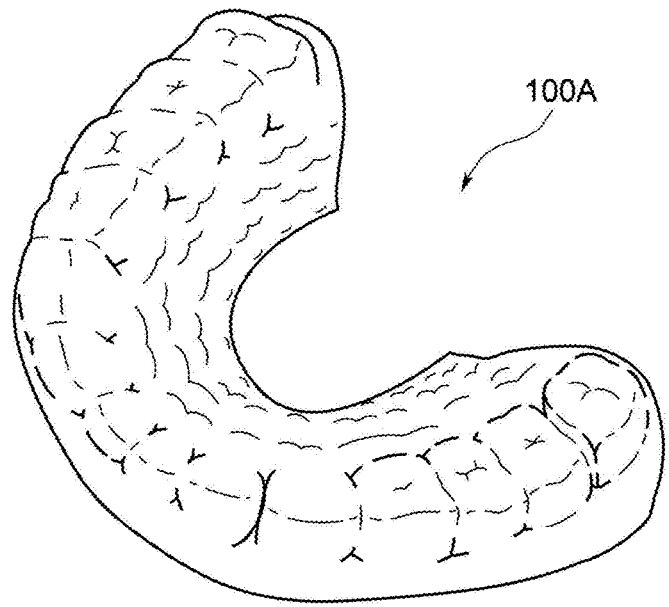

First, as illustrated in FIG. 4(a), a model 200 having a reconstructed shape of the oral cavity of a patient is prepared by a known method. Here, as illustrated in the figure, an example in which a gap is formed between a back tooth located at an innermost position in the oral cavity and a tooth adjacent to the back tooth is shown. Next, as illustrated in FIG. 4(b), a grip member 100A is formed of, for example, a resin material to have a shape fitting to the model. That is, the grip member 100A is formed to fit to an inner shape of the oral cavity of a patient so as to grip and cover a tooth row, gum parts, and alveolar bone parts of the patient. Specifically, the grip member 100A covers the tooth row, the gum parts and the alveolar bone parts on the buccal side and the lingual side of the tooth row (note that as described above, it is sufficient that the grip member 100A covers at least an area extending from the crown part to the periphery of the cervical part).

Figure 5A:
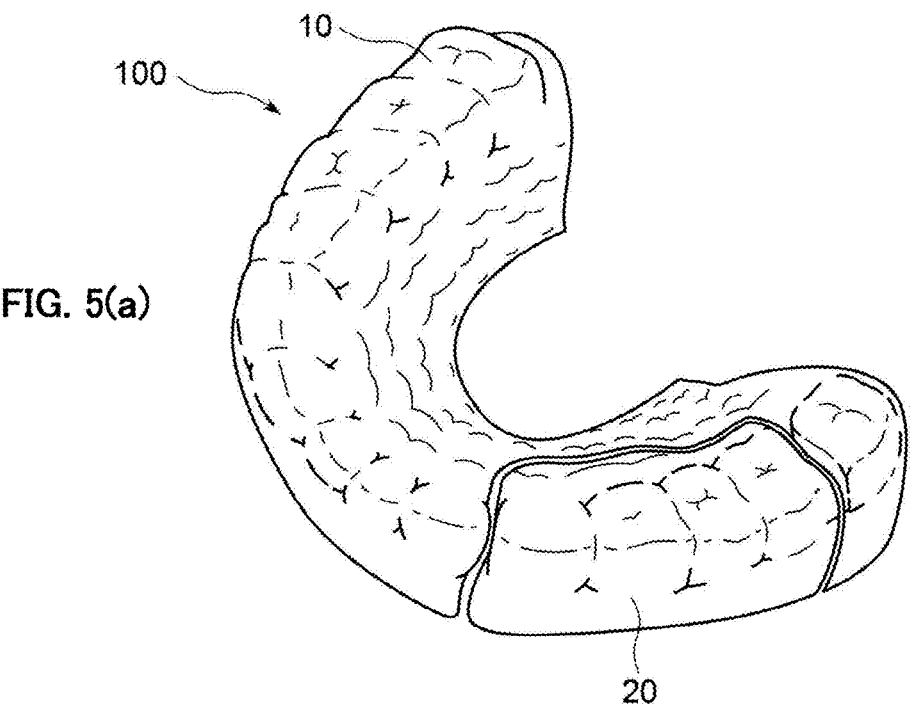
FIGS. 5(a) and 5(b) are views illustrating steps in the method of manufacturing the correction device according to the embodiment of the present invention.

Next, as illustrated in FIG. 5(a), the grip member 100A is cut into a first piece 20 and a second piece 10 which are separated and independent of each other. Specifically, the grip member 100A is divided into the first piece 20 which grips and covers at least an area extending from the crown part to the cervical part of the correction target tooth 50 and the second piece 10 which grips and covers at least an area extending from the crown part to the periphery of the cervical part of the non-target tooth.

Figure 5B:
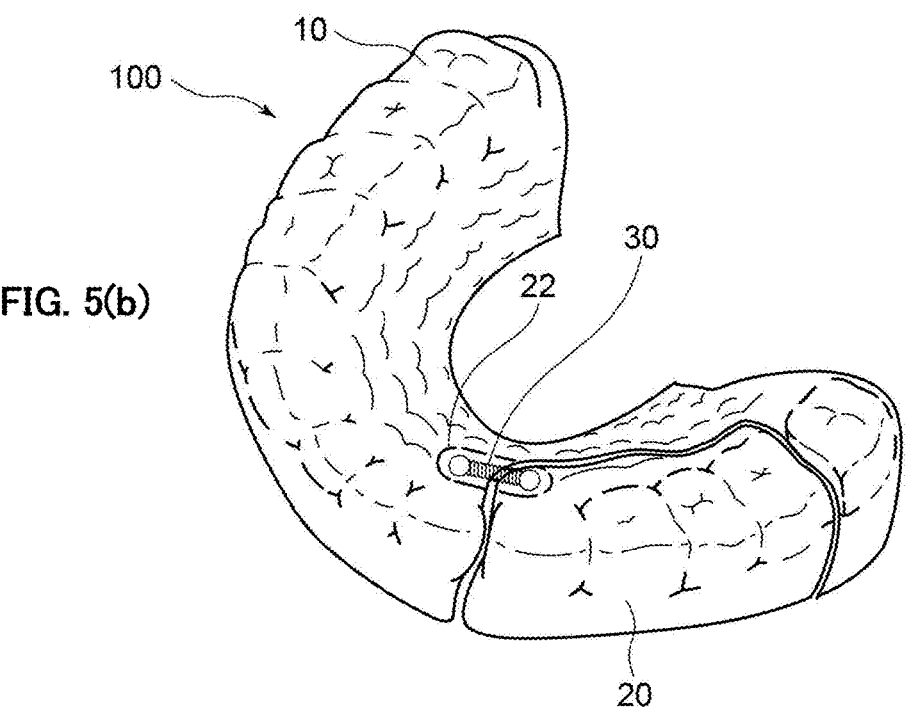

Then, as illustrated in FIG. 5(b), a force applying member 30 which moves the correction target tooth 50 in a desired direction is provided on the first piece 20 and the second piece 10 to connect the first piece 20 to the second piece 10. The force applying member 30 is provided, so that portions of the first piece 20 and the second piece 10 on which the force applying member 30 is provided have a greater thickness than the other portions the first piece 20 and the second piece 10, and the portions having the greater thickness are thick portions 22. Thus, the correction device 100 according to the present embodiment is formed.

In the above-described embodiment, the grip member including the first piece 20 and the second piece 10 can be made of, for example, a resin material having a thickness of 0.2 mm-0.8 mm. When the grip member has such a thickness, patients feels as little discomfort as when known aligners are used. In the case of known aligners, as described in the technical problem, permanent deformation may be caused, and the aligners may not satisfactorily function as an anchorage due to the permanent deformation. However, the grip member according to the present embodiment is divided into the first piece 20 and the second piece 10, so that no permanent deformation is caused as in the case of the known aligners, and the grip member can satisfactorily function as an anchorage. On the other hand, the grip member including the first piece 20 and the second piece 10 can be made of, for example, a resin material having a thickness greater than or equal to 2 mm. Also in this case, permanent deformation is not caused, and the grip member can more stably function as an anchorage and can be used as an aligner.

The correction device 100 according to the present embodiment having the configuration described above provides the following advantages. That is, the first piece 20 included in the grip member covers at least an area extending from the crown part to the periphery of the cervical part of the correction target tooth 50 to grip the correction target tooth 50, and the second piece 10 included in the grip member and independent of the first piece 20 covers and grips at least an area extending from the crown part to the periphery of a cervical part of the non-target teeth except the correction target tooth 50. With this configuration, the second piece 10 serves as a strong anchorage. Therefore, by using the force applying member 30 provided to connect the first piece 20 to the second piece 10, the correction target tooth 50 gripped by the first piece 20 can be moved in a desired direction. At this time, since the second piece 10 serves as a strong anchorage, the non-target teeth gripped by the second piece 10 are prevented from being moved by reaction force of the force applied to the correction target tooth 50 gripped by the first piece 20. Since the second piece 10 serves as a strong anchorage, providing the force applying member 30 at a suitable position allows the movement of the correction target tooth 50 not only in a desired direction, i.e., in the buccal-lingual direction but also in a distal direction and a mesial direction which are conventionally difficult directions and also in upward and downward directions. Moreover, the first piece 20 covers at least an area extending from the crown part to the periphery of the cervical part of the correction target tooth 50. Therefore, the force by the force applying member 30 is applied to not only the crown portion of the correction target tooth 50 but also the entire region to the cervical part. Thus, the horizontal movement but not the inclination movement of the correction target tooth 50 is easily performed. The correction target tooth 50 is not moved by using the property of the grip member itself while the anchorage is ensured. While the anchorage is ensured, the force applying member 30 which is independent of the grip member including the first piece 20 and the second piece 10 moves the correction target tooth 50. Therefore, it is possible to ensure the movement of the correction target tooth 50 in a desired direction. Therefore, with the correction device 100 according to the present embodiment, it is possible to easily achieve and ensure not only the buccal/lingual movement but also the distal/mesial movement of the correction target tooth 50 while the anchorage is satisfactorily ensured, so that highly predictable treatment can be achieved. When the correction device 100 according to the present embodiment is used on the upper jaw side, the second piece 10 has the palate portion 15. The palate portion 15 is continuous with a part covering the alveolar bone part located on the lingual side of the tooth row, and is formed to fit to the shape of the palate, so that more stable anchorage can be ensured. Even when the correction device 100 is changed due to step up, a post-aligned tooth is used together with an existing anchorage so as to be a new anchorage, so that it is possible to set a new second piece 10 serving as a more stable anchorage. With this configuration, the new second piece 10 can also serve as a retainer to prevent the post-aligned tooth from returning to its pre-alignment position.

Next, variations of the correction device 100 according to the present embodiment will be described.

Figure 6A:
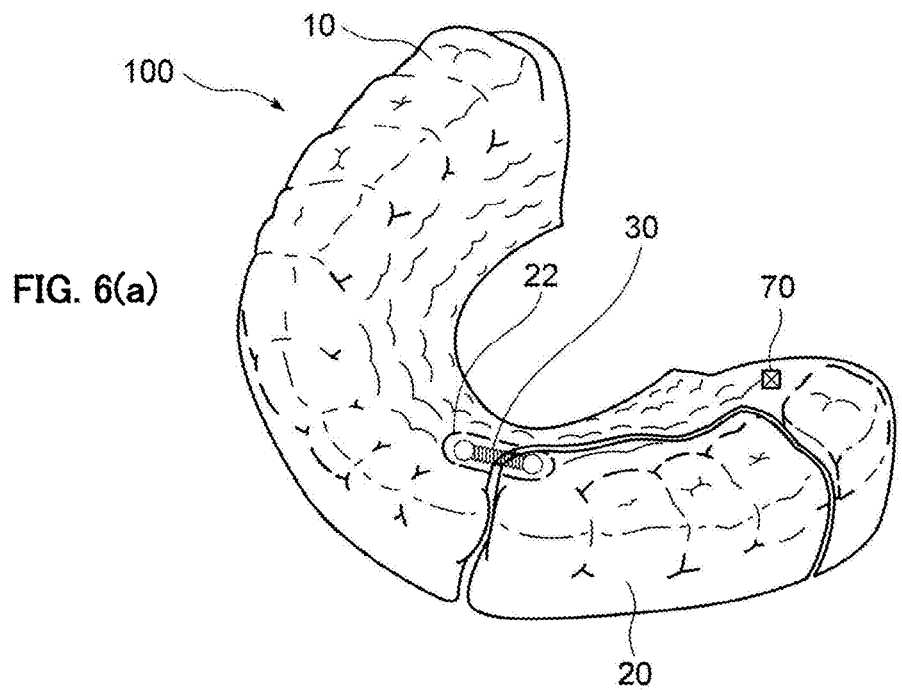
FIGS. 6(a) and 6(b) are views illustrating a variation of the structure of the correction device according to the embodiment of the present invention, wherein a skeletal anchor is used.
Figure 6B:
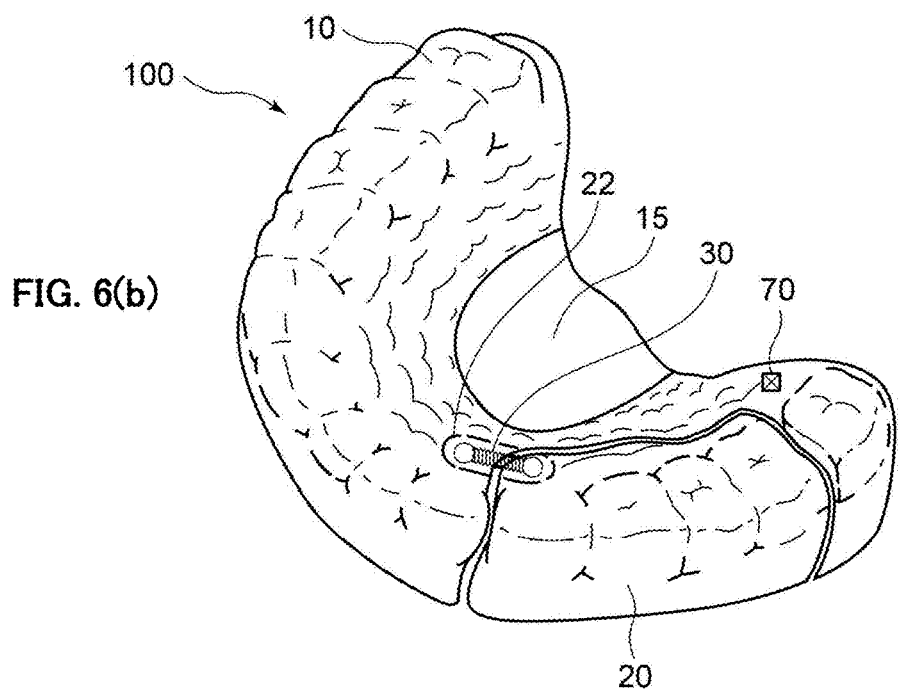

FIGS. 6(a) and 6(b) illustrate variations of the correction device 100 according to the embodiment of the present invention. Specifically, an example structure is shown in which a skeletal anchor 70 is further provided in the structure of the correction device 100 illustrated in FIGS. 1(a) and 1(b). FIG. 6(a) shows the correction device 100 used on the lower jaw side, and FIG. 6(b) shows the correction device 100 used on the upper jaw side.

As illustrated in FIGS. 5(a) and 5(b), the correction device 100 according to the present embodiment can be used in a form in which the skeletal anchor 70 is implanted in the second piece 10 at the periphery of the back teeth. The skeletal anchor 70 is, for example, a mini screw or an implant passing through the second piece 10.

Thus, the mini screw or the implant which serves as a definitive anchorage is implanted in the second piece 10, so that the second piece 10 serves as a stable and definitive anchorage. Thus, the correction target tooth 50 gripped by the first piece 20 can be more reliably moved in a desired direction. Cases subjected surgical orthodontics such as osteotomy involving high risks can be reduced as much as possible. The skeletal anchor 70 can be in a variety of shapes, but a square shape which is barely rotated by applied force, as illustrated in the figure, is preferable so that the skeletal anchor 70 serves as more stable anchorage.

Figure 7:
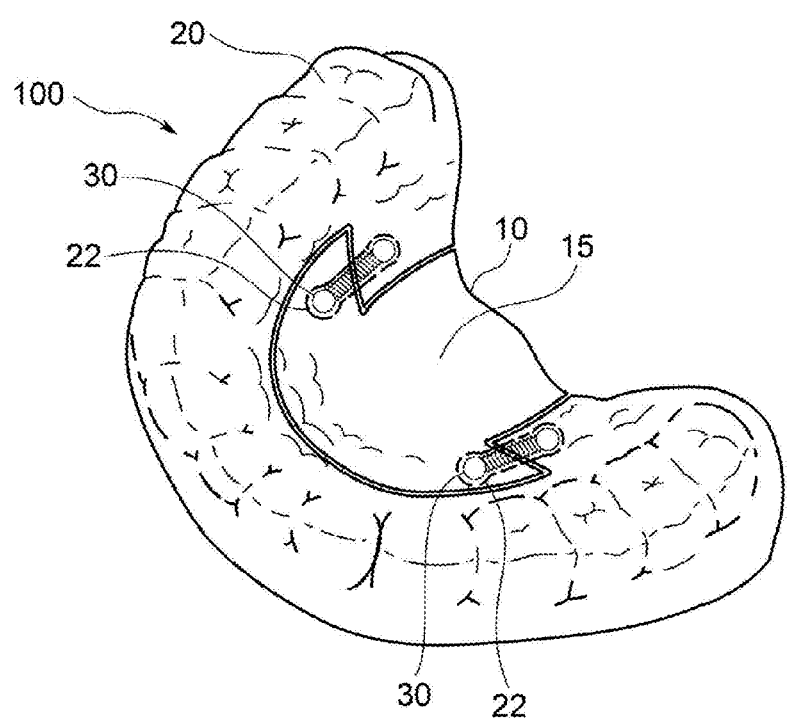
FIG. 7 is a view illustrating a variation of the structure of the correction device according to the embodiment of the present invention, wherein the entire tooth row is moved, and the correction device is used on the upper jaw side.

FIG. 7 illustrates a variation of the structure of the correction device 100 according to the embodiment of the present invention. Specifically, an example structure of the correction device 100 according to the present embodiment for moving the entire tooth row is illustrated, wherein the correction device 100 is used on the upper jaw side.

As illustrated in FIG. 7, the first piece 20 covers the entire row of the correction target tooth 50, whereas the second piece 10 does not cover the tooth row itself In this case, in order to move the entire tooth row by the force applying member 30, for example, the first piece 20 covers the entire tooth row, and the second piece 10 covers portions other than those covered with the first piece 20. Specifically, the second piece 10 covers an area extending from the periphery of a cervical part to a gum portion, and a peripheral region of an alveolar bone of a peripheral region of back teeth of the grip member (a peripheral region of the back teeth on the lingual side of the grip member). The force applying member 30 is provided to extend over a portion of the first piece 20 corresponding to a region in the periphery of a cervical part to a gum portion, a peripheral region of an alveolar bone of a peripheral region of back teeth and a portion of the second piece 10 corresponding to a region in the periphery of a cervical part to a gum portion, and a peripheral region of an alveolar bone of a peripheral region of back teeth adjacent to the portion of the first piece 20. With this configuration, the entire tooth row gripped by the first piece 20 can be moved in mesial-distal directions. Placing the force applying member 30 at a suitable position allows the entire tooth row to move not only in mesial-distal directions but also in left-right directions. As described above, in the correction device 100 according to the present embodiment, the second piece 10 is used as anchorage, so that all the teeth gripped by the first piece 20 can be moved in a desired direction by using the force applying member 30. That is, the entire tooth row inclusive of the alveolar bone of a patient can be moved in desired directions to the front, rear, left, and right (e.g., buccal-lingual directions, distal-mesial directions) with respect to the cranial bone and the jawbone. Therefore, bimaxillary protrusion, bimaxillary overgrowth and underdevelopment can be treated, so that physical and aesthetic stress caused when conventional facial masks or headgears are used can be significantly reduced. In particular, in a conventional method, i.e., a facial mask or a headgear for moving the entire tooth row, the entire tooth row can be moved in mesial-distal directions, but a tooth row displaced in the left or right direction due to behavior, etc. cannot be moved to the right or left direction. The correction device 100 according to the present embodiment allows movement in right-left directions which is conventionally difficult.

Figure 8A:
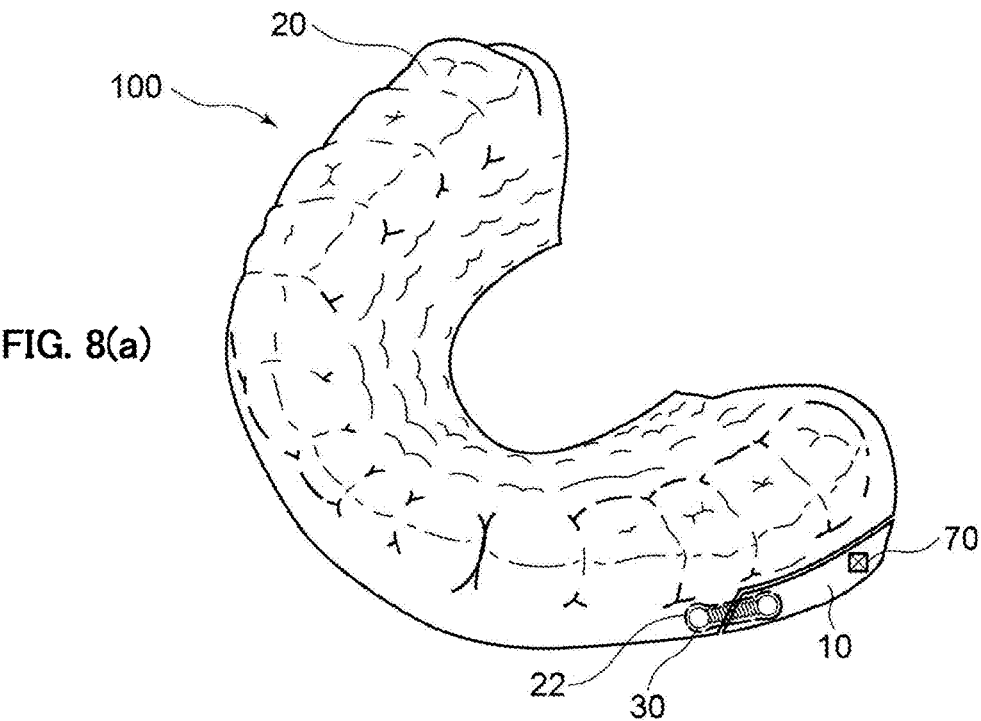
FIGS. 8(a) and 8(b) are views illustrating a variation of the structure of the correction device according to the embodiment of the present invention, wherein the entire tooth row is moved using the skeletal anchor together with the correction device.
Figure 8B:
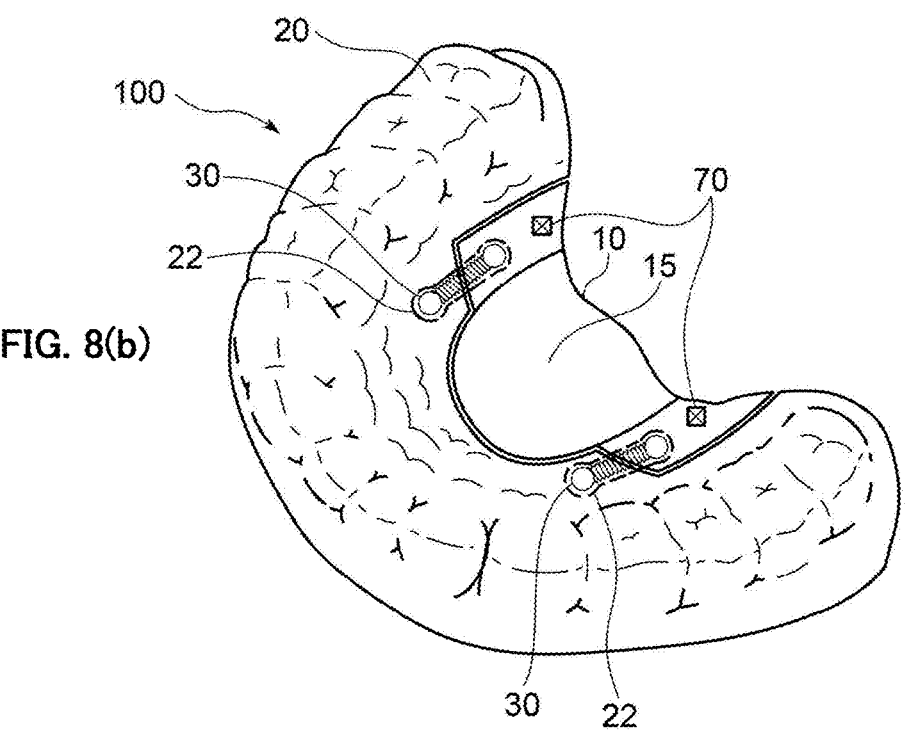

FIGS. 8(*a*) and 8(*b*) illustrate a variation of the structure of the correction device 100 according to the embodiment of the present invention. Specifically, an example structure is shown in which a skeletal anchor 70 is further provided in the structure of the correction device 100 illustrated in FIG. 7. FIG. 8(*a*) shows the correction device 100 used on the lower jaw side, and FIG. 8(*b*) shows the correction device 100 used on the upper jaw side.

As illustrated in FIGS. 8(*a*) and 8(*b*), the correction device 100 according to the present embodiment can be used in a form in which the skeletal anchor 70 is implanted in the second piece 10. The skeletal anchor 70 is, for example, a mini screw or an implant passing through the second piece 10. The skeletal anchor 70 is preferably implanted at a portion of the second piece 10, for example, in the case of FIG. 8(*a*), a portion in the periphery of back teeth of the buccal side portion of the grip member, and for example, in the case of FIG. 8(*b*), a portion in the periphery of back teeth of the lingual side portion of the grip member. In the example of FIG. 8(*a*), a structure in which the second piece 10, the force applying member 30, and the skeletal anchor 70 are formed at the back teeth on one side is illustrated in the figure, a similar structure (not shown) is also formed at the back teeth on the other side.

Thus, the mini screw or the implant which serves as a definitive anchorage is implanted in the second piece 10 (including the palate portion 15), so that the second piece 10 serves as a stable and definitive anchorage. Thus, it is possible to ensure the movement of the entire tooth row gripped by the first piece 20 in the left-right directions and in the distal-mesial directions with respect to the cranial bone and the jawbone. Cases subjected surgical orthodontics such as osteotomy involving high risks can be reduced as much as possible. In setback movement of the entire tooth row by a currently trialed method in which a multi-bracket is used together with a skeletal anchor, force is obliquely exerted, so that three dimensional misalignment may be caused, and forward and lateral movement is currently impossible. However, in the correction device 100 according to the present embodiment, no three dimensional misalignment is caused, and the forward and lateral movement is also possible.

Figure 9A:
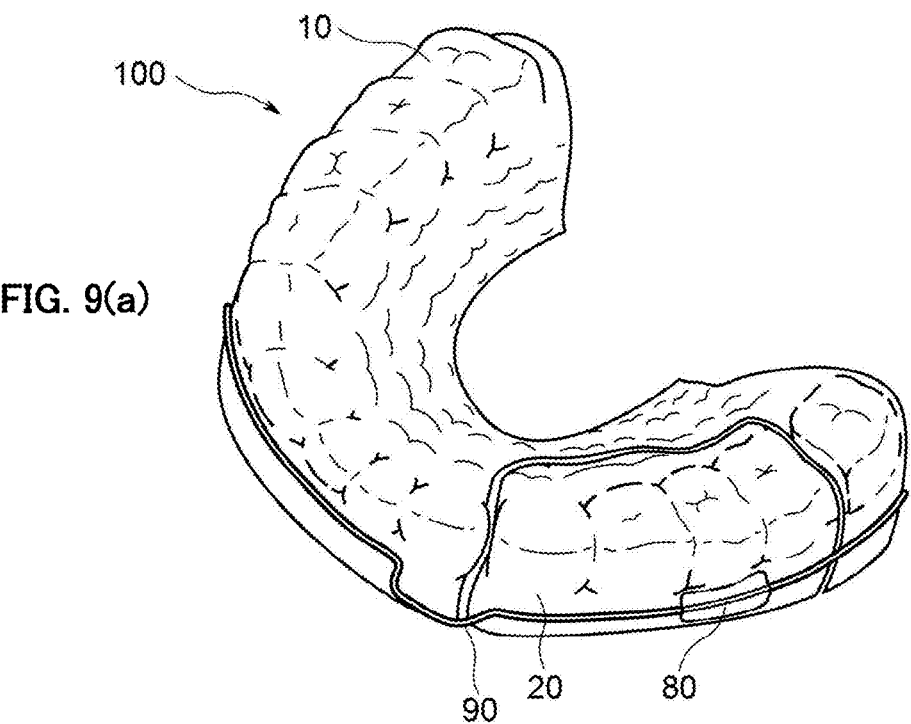
FIGS. 9(a) and 9(b) are views illustrating a variation of the structure of the correction device according to the embodiment of the present invention, wherein a wire is used instead of a screw.
Figure 9B:
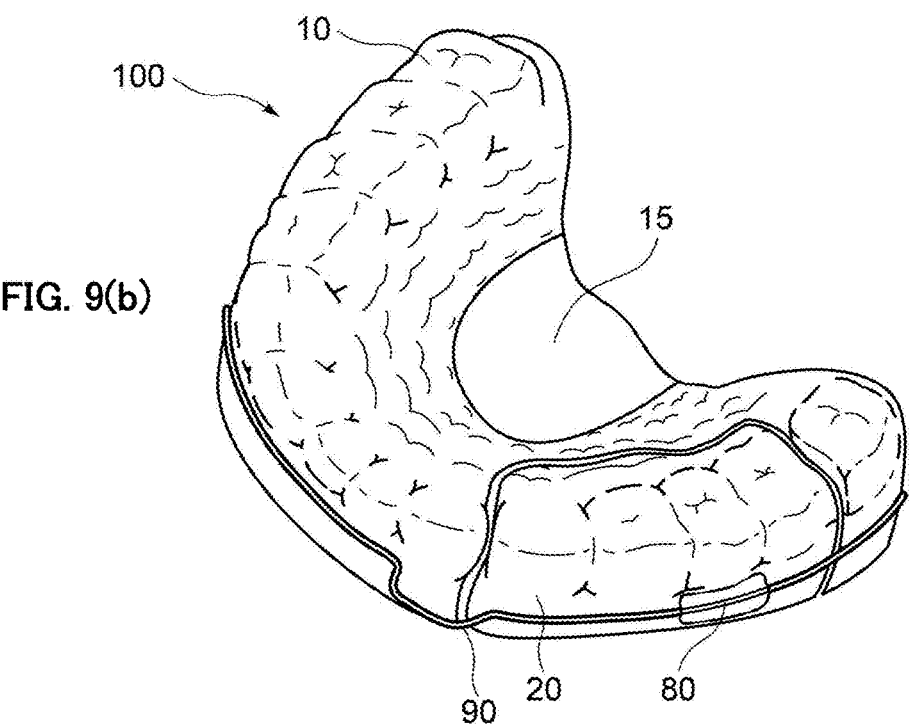

FIGS. 9(*a*) and 9(*b*) illustrate a variation of the structure of the correction device 100 according to the embodiment of the present invention. Specifically, an example structure is illustrated in which instead of the screw as the force applying member 30 of the correction device 100 illustrated in, for example, FIGS. 1(*a*) and 1(*b*), a wire 90 serving as a force applying member is used, wherein FIG. 9(*a*) shows the correction device 100 used on the lower jaw side, and FIG. 9(*b*) shows the correction device 100 used on the upper jaw side.

As illustrated in FIGS. 9(*a*) and 9(*b*), the wire 90 covers the first piece 20 and the second piece 10. The wire 90 is attached to the first piece 20 by, for example, an adhesive 80. The shape of the wire 90 is adjusted in advance so that force using return force is exerted on the correction target tooth 50 gripped by the first piece 20 moves in a desired direction in which the correction target tooth 50 is to be moved. With this configuration, even with the correction device 100 using the wire 90 as in the present embodiment, the second piece 10 serves as a strong anchorage, so that advantages similar to those described above can be obtained by using the returning force of the wire 90.

FIGS. 10(*a*) and 10(*b*) illustrate a variation of the structure of the correction device 100 according to the embodiment of the present invention. Specifically, an example structure is illustrated in which a region of the second piece 10 covering the outside of the tooth row is large as compared to that of the second piece 10 of the correction device 100 illustrated in, for example, FIGS. 1(*a*) and 1(*b*), wherein FIG. 10(*a*) shows the correction device 100 used on the lower jaw side, and FIG. 10(*b*) shows the correction device 100 used on the upper jaw side.

Figure 10A:
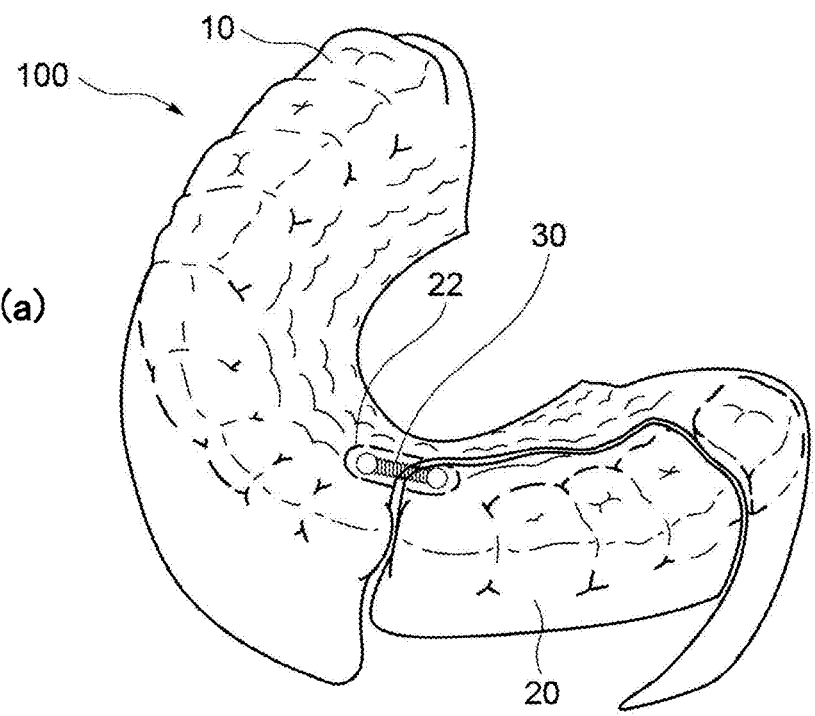
FIGS. 10(a) and 10(b) are views illustrating a variation of the structure of the correction device according to the embodiment of the present invention, wherein a region covering the outside of the tooth row is large.
Figure 10B:
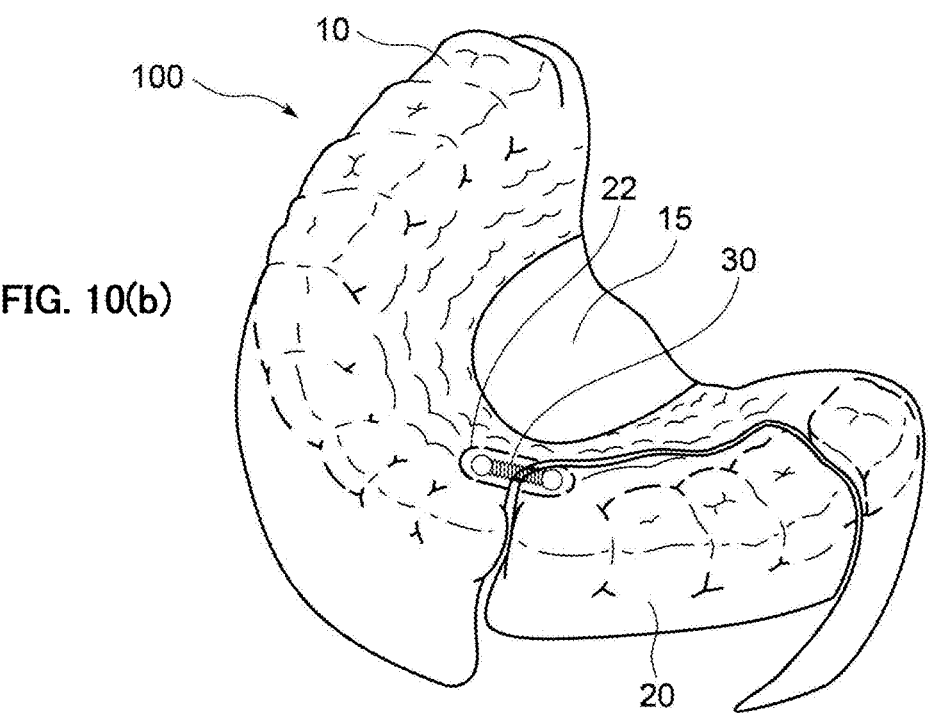

As illustrated in each of the figures such as FIGS. 1(*a*) and 1(*b*), when the grip member including the first piece 20 and the second piece 10 of the correction device 100 according to the present embodiment covers, on the buccal side of the tooth row, at least an area extending from the crown part to the periphery of the cervical part, more specifically, the tooth row, the gum part, and highest contour portions of the alveolar bone part, it is possible to obtain a strong anchorage as described above. However, as illustrated in FIGS. 10(a) and 10(b), the grip member including the first piece 20 and the second piece 10 of the correction device 100 may also cover, on the buccal side of the tooth row, a lower portion of the alveolar bone part so that the force of the grip member as the anchorage is further enhanced as compared to the grip member of the correction device 100 illustrated in, for example, FIGS. 1(a) and 1(b). In this case, placing the correction device 100 may be difficult or cause pain depending on the oral shape of a patient. Therefore, the downward length of the grip member may be accordingly adjusted. The present variation is applicable to any of the correction devices described above.

Figure 11A:
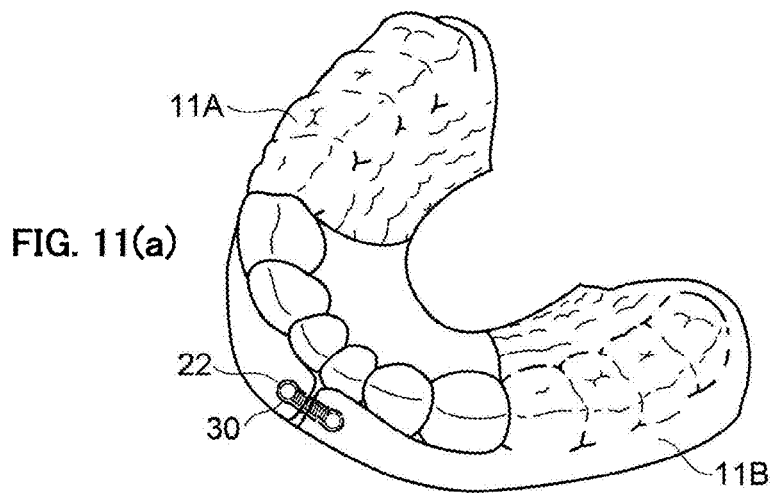
FIGS. 11(a)-11(c) are views illustrating a variation of the structure of correction devices according to an embodiment of the present invention, wherein a first piece and a second piece are formed to have the same size so that tooth rows facing each other are moved together to the buccal side or the lingual side by applying opposite forces exerted by the force applying member.
Figure 11B:
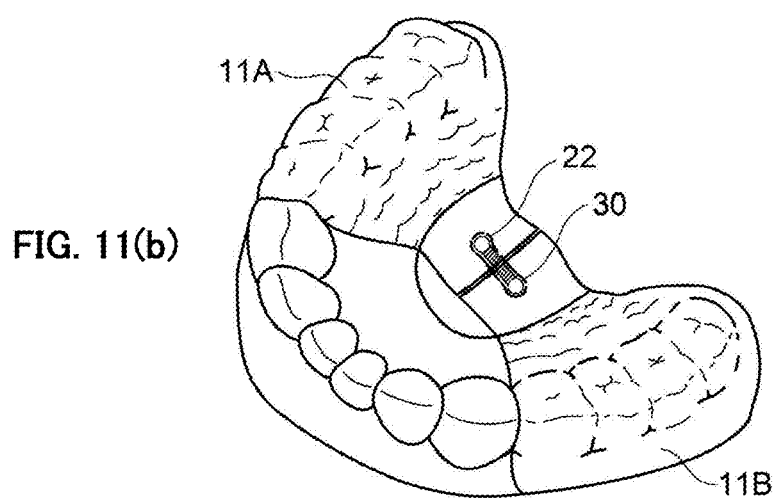
Figure 11C:
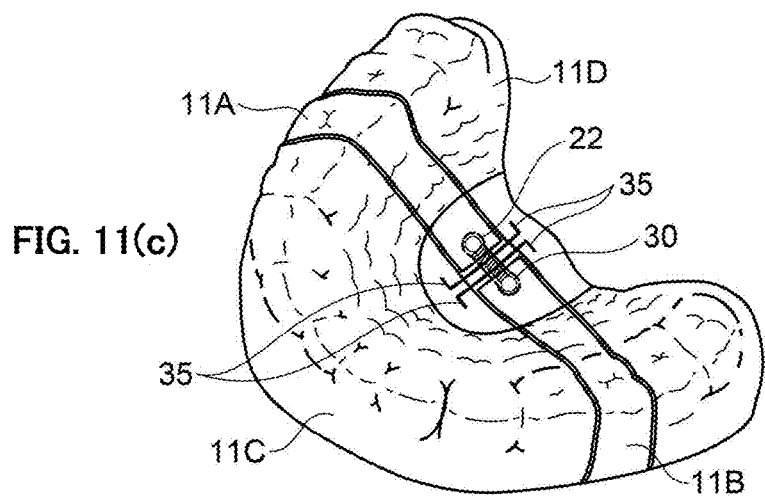

FIGS. 11(a)-11(c) illustrate variations of the structure of the correction device 100 according to an embodiment of the present embodiment. Specifically, a first piece and a second piece are formed to have the same size so that tooth rows facing each other are moved together to the buccal side or the lingual side by applying opposite forces exerted by the force applying member, wherein FIG. 11(a) shows a correction device 100 used on the lower jaw side, FIG. 11(b) shows a correction device 100 used on the upper jaw side, and FIG. 11(c) shows a correction device 100 in which fixing members drawn out of the force applying member is provided on the grip member close thereto.

In FIG. 11(a), a first piece 11A grips, for example, four teeth from the back on one side as correction target teeth to cover an area extending from the crown part to the periphery of the cervical part of the tooth row of a patient. The second piece 11B grips, for example, four teeth from the back on the other side as correction target teeth to cover a region from a crown part to a periphery of a cervical part of the tooth row of the patient. The correction device 100 is used for the lower jaw. Therefore, the first piece 11A and the second piece 11B extend to a position near front teeth. The force applying member 30 is arranged at a position near the front teeth.

In FIG. 11(b), a first piece 11A grips correction target teeth to cover an area extending from the crown part to the periphery of the cervical part of the tooth row of a patient. The second piece 11B grips correction target teeth different from the above-described correction target tooth to cover an area extending from the crown part to the periphery of the cervical part of the tooth row of the patient. The correction device is used for the upper jaw. Therefore, the force applying member 30 is provided at a palate portion.

In the configuration of each of FIGS. 11(a)-11(c), both of the first piece 11A and the second piece 11B of the grip member covers an area extending from the crown part to the periphery of the cervical part of the correction target tooth to grip the correction target teeth. Therefore, while the first piece 11A and the second piece 11B are used as strong anchorages, the correction target teeth gripped by the first piece 11A and the second piece 11B can be moved in a desired direction by using opposite forces exerted by the force applying member. Moreover, both of the first piece 11A and the second piece 11B are strong anchorages, which prevents movement caused by reaction force of the force applied to the gripped correction target teeth. The correction target teeth are easily moves not obliquely but horizontally. The correction target teeth can be reliably moved in a desired direction by using the force applying member. In particular, the present embodiment is more suitable when the correction target teeth gripped by the first piece 11A and the correction target teeth gripped by the second piece 11B are symmetrical positional relationship. However, the present invention is not limited to the present embodiment, and similar correction is possible by accordingly modifying the design of the grip member.

In the configuration of FIG. 11(c) which shows a configuration basically similar to that shown in FIG. 11(b), but when a small number of teeth gripped by the first piece 11A and the second piece 11B, a third piece 11C and a fourth piece 11D independent of the first piece 11A and the second piece 11B are provided near the first piece 11A and the second piece 11B. The force applying member 30 includes fixing members 35 extending from the force applying member 30 to the third piece 11C and the fourth piece 11D. That is, each fixing member 35 extends from a region extending over the first piece 11A and the second piece 11B to a corresponding one of the third piece 11C and the fourth piece 11D. With this configuration, a stronger anchorage can be obtained.

Figure 12A:
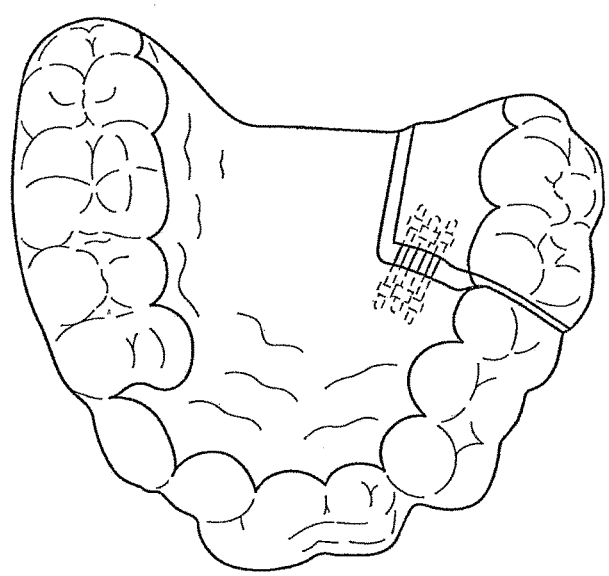
Figure 12B:
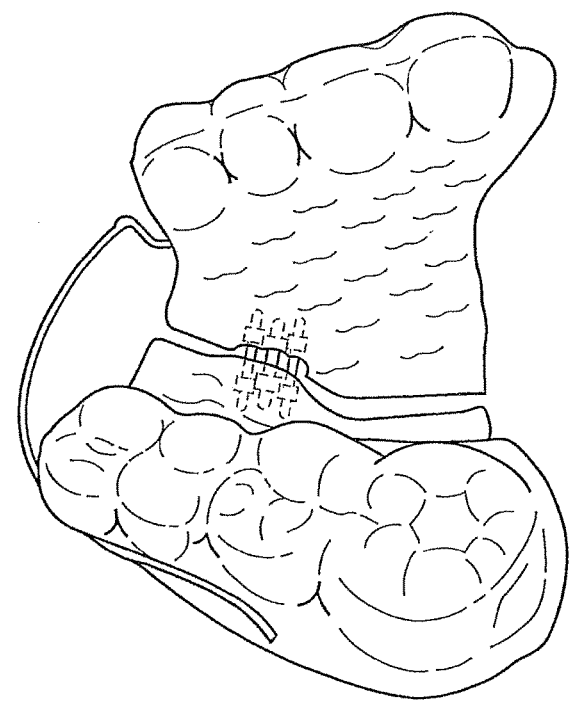
Figure 18A:
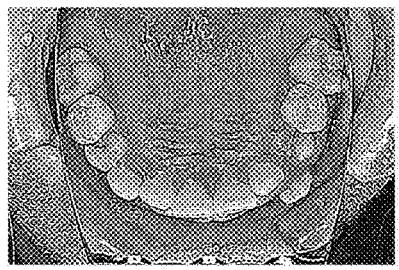
FIGS. 18(a)-18(d) are views illustrating case 1 in which a correction device according to an embodiment of the present invention is used.
Figure 18B:
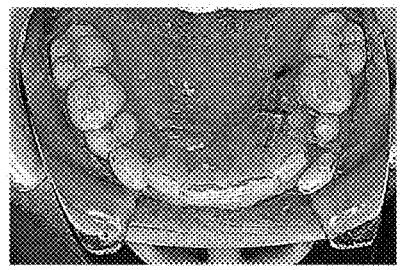
Figure 18C:
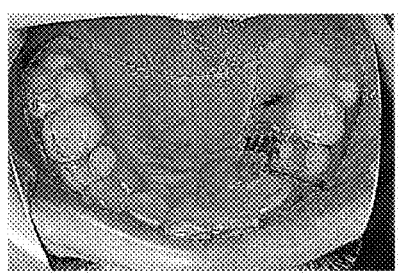
Figure 18D:
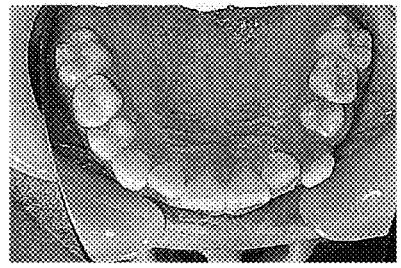
Figure 19A:
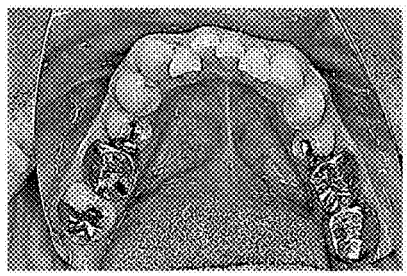
FIGS. 19(a)-19(d) are views illustrating case 2 in which a correction device according to an embodiment of the present invention is used.
Figure 19B:
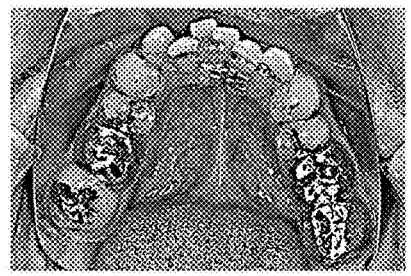
Figure 19C:
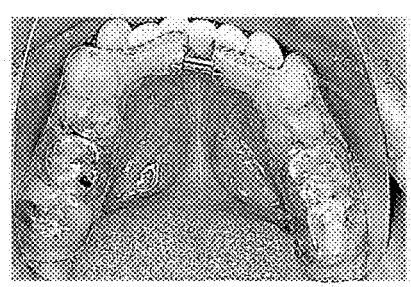
Figure 19D:
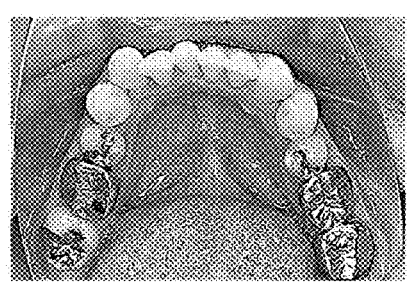

Here, FIGS. 12(a) and 12(b) show examples of the correction device 100 according to an embodiment of the present embodiment. FIG. 12(a) shows an example of a correction device similar to a correction device illustrated in FIGS. 18(b) and 18(c) relating to case 1 which will be described later, wherein two teeth from the back are moved by using a correction device used on the upper jaw side. FIG. 12(b) shows an example of a correction device similar to that of FIG. 11(b), wherein FIG. 12(b) shows an example in which the correction device used on the upper jaw side is divided at the center thereof so that a first piece and a second piece of a grip member are formed to have the same size, so that opposite forces are applied to tooth rows facing each other by the force applying member, and tooth rows on the left and on the right are moved together by the same distance. In this case, a conventional expansion plate causes oblique movement, but the present invention allows horizontal movement. At the same time, the present invention also allows compression of left and right tooth rows which was difficultly realized by removable-type appliances. The present invention also allows horizontal movement. Note that FIG. 12(b) shows an example in which a wire is attached to also correct the peripheral portion of front teeth.

Figure 13A:
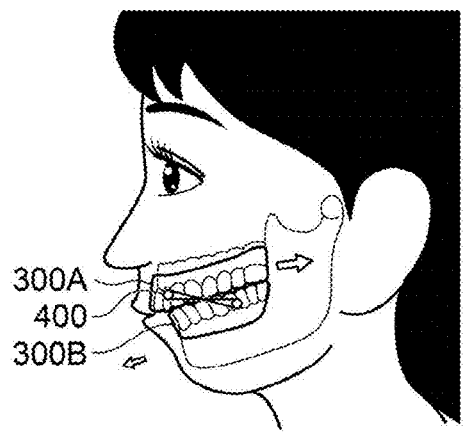
FIGS. 13(a)-13(c) are views illustrating a variation of the structure of the correction device according to an embodiment of the present invention, wherein the views each show an example structure in which a grip member is placed on each of the upper jaw side and the lower jaw side.
Figure 13B:
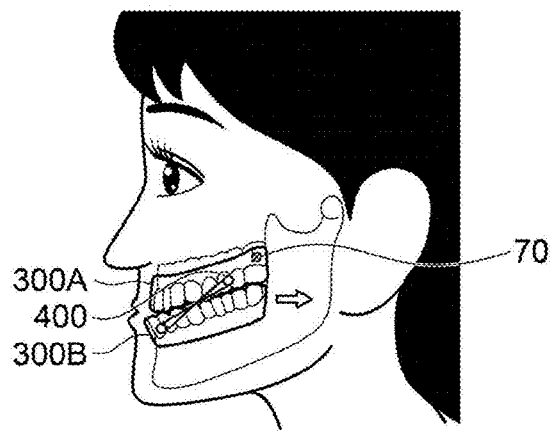
Figure 13C:
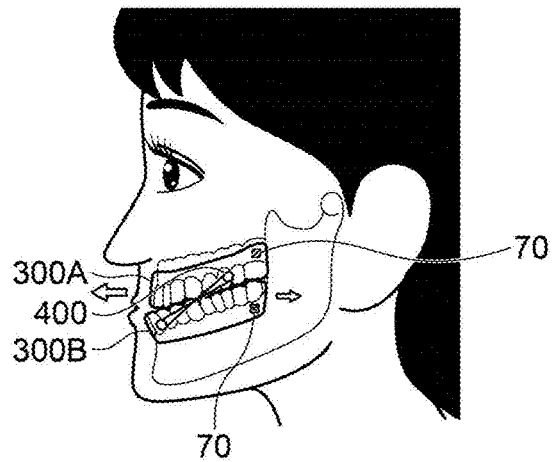

FIGS. 13(a)-13(c) illustrate variations of the structure of a correction device according to an embodiment of the present embodiment. Specifically, an example of the structure in which a grip member is placed on each of the upper jaw side and the lower jaw side is illustrated.

FIG. 13(a) shows an example in which lower jaw underdevelopment or upper jaw overgrowth is corrected without using a skeletal anchor. As illustrated in the figure, a first piece 300A which is the grip member described above is used for the upper jaw, and covers an area extending from the crown part to the periphery of the cervical part of the entire tooth row of the upper jaw of a patient. Similarly, a second piece 300B which is the grip member is used for the lower jaw, and covers a region from a crown part to a periphery of a cervical part of the entire tooth row of the lower jaw of the patient. The first piece 300A and the second piece 300B are connected to each other by an intermaxillary rubber 400 serving as the force applying member 30. Note that the intermaxillary rubber 400 may be attached to projections, which have for example, a button shape and are provided on the first piece 300A and the second piece 300B.

With this configuration, when the upper jaw is overgrown, the lower jaw is underdeveloped, and the tooth row of the upper jaw and the tooth row of the lower jaw are not in alignment with each other, the intermaxillary rubber 400 is accordingly used to apply stronger force to the upper jaw side than to the lower jaw side, thereby pulling the upper jaw in the arrow direction in the figure to the right in the plane of the paper, so that the misalignment due to projection of the upper jaw can be easily corrected.

As illustrated in FIG. 13(b), a skeletal anchor 70 is implanted in the grip member on the upper jaw side. Therefore, when the lower jaw is overgrown and the tooth row of the upper jaw and the tooth row of the lower jaw are not in alignment with each other, the lower jaw is moved by being pulled in the arrow direction in the figure by appropriately using the intermaxillary rubber 400 with the upper jaw serving as an anchorage, so that the misalignment due to projection of the lower jaw can be easily corrected.

Although not illustrated in FIG. 13(b), the skeletal anchor 70 can be implanted only in the grip member on the lower jaw side. For example, when the upper jaw which is anatomically instable is to be moved, in particular, when the upper jaw is underdeveloped, the upper jaw can be moved by being pulled out with the lower jaw serving as an anchorage.

In FIG. 13(c), skeletal anchors 70 are implanted in grip members on the upper jaw side and the lower jaw side. Thus, the intermaxillary rubber 400 serves as a member applying opposite forces, and growth promotion/growth inhibition of the entire the jawbone and the facial bone including the entire tooth row fixed by the skeletal anchors 70 is possible. Depending on the direction in which the intermaxillary rubber is attached, growth promotion/growth inhibition of the upper jawbone and the face bone around the upper jaw bone or growth promotion/growth inhibition of the lower jawbone and the face bone around the lower jaw bone is possible. In FIG. 13(c), stronger force is applied to the upper jaw side than to the lower jaw side, thereby performing the growth inhibition of the lower jawbone and the facial bone near the lower jawbone in the arrow direction in the figure to the left in the plane of the paper.

As described above, when a patient has an overgrown or underdeveloped upper jaw, an overgrown or underdeveloped lower jaw, and the tooth row of the upper jaw and the tooth row of the lower jaw are not in alignment with each other, the misalignment can be easily corrected by using, for example, an intermaxillary rubber as a force applying member. In particular, when the upper jaw is overgrown and the lower jaw is underdeveloped, or when the upper jaw is underdeveloped and the lower jaw is overgrown, the misalignment between the upper jaw and the lower jaw can be effectively corrected without using the skeletal anchor, and when the skeletal anchor is used, growth promotion/growth inhibition of the entire the jawbone and the facial bone including the entire tooth row is possible.

Figure 14A:
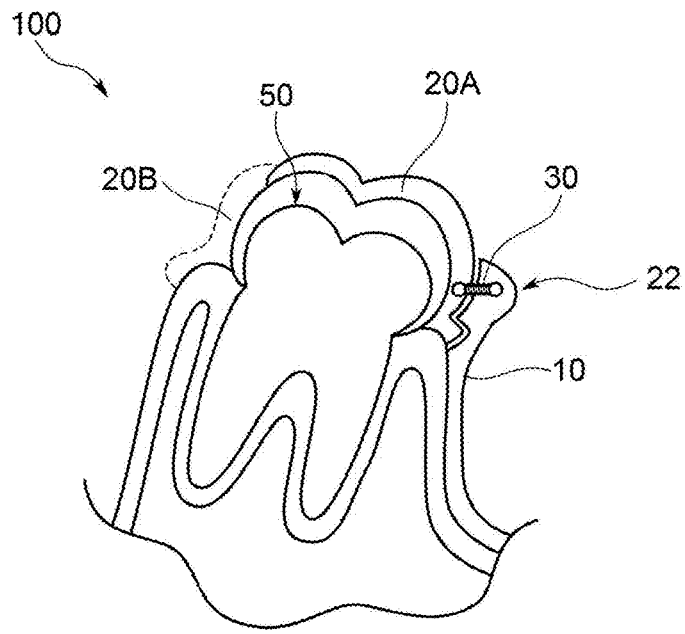
FIG. 14(a) is a cross sectional view illustrating an example structure of the correction device according to the embodiment of the present invention, wherein a correction target tooth is obliquely moved.

FIG. 14(a) illustrates an example structure when a correction target tooth is obliquely moved by the correction device 100 according to the embodiment of the present invention.

As illustrated in FIG. 14(a), in the case where a correction target tooth 50 itself is inclined from the vertical direction, if the correction target tooth 50 is moved by, for example, the correction device 100 illustrated in FIG. 2(b), the correction target tooth 50 horizontally moves with the correction target tooth 50 being inclined. Therefore, when the correction target tooth 50 itself is inclined from the vertical direction as illustrated in FIG. 14(a), a first piece 20A is preferably used in order to move the correction target tooth 50 in the vertical direction. The first piece 20A has such a shape that an outer portion 20B corresponding to a crown part of the tooth row is, for example, removed, or is not formed. With this configuration, the gripping force applied to the correction target tooth 50 by the first piece 20A is weak at the outer portion of the correction target tooth 50. Therefore, the correction target tooth 50 inclined to the right from the vertical direction can be inclined leftward so that the correction target tooth 50 stands along the vertical direction.

Figure 14B:
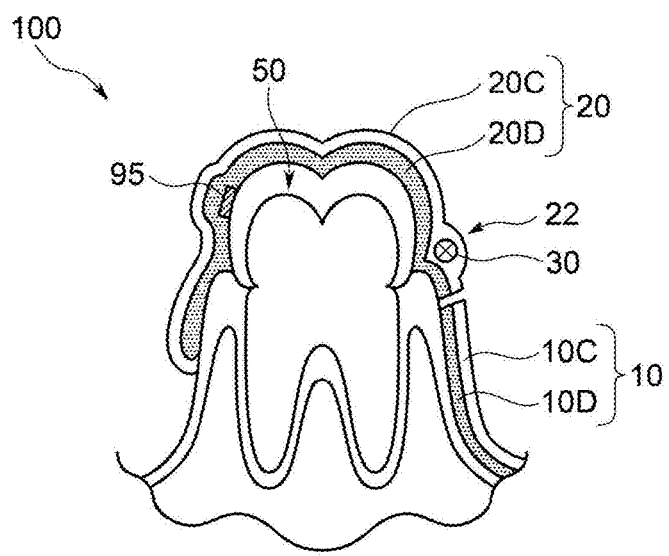
FIG. 14(b) is a cross-sectional view illustrating an example of the structure of the correction device according to the embodiment of the present invention, wherein a grip member has a two-layer structure including a lower layer and an upper layer.

FIG. 14(b) illustrates an example structure in which the grip member of the correction device 100 according to the embodiment of the present invention has a two-layer structure including a lower layer and an upper layer.

As illustrated in FIG. 14(b), when for example, a fixed-type multi-bracket is placed on a tooth row, the grip member preferably includes a lower layer (a lower layer 20D of a first member 20, a lower layer 10D of a second member 10) made of a silicon membrane sheet and an upper layer (a upper layer 20C of a first member 20, a upper layer 20D of a second member 10) made of a resin.

With this configuration, the grip member can be used together with, for example, a fixed-type multi-bracket. That is, when a wire is placed on the entire tooth row by, for example, a button 95, the correction target tooth 50 can be moved as described above by the correction device 100 with the multi-bracket covered with the silicon membrane sheets 20D, 10D which are lower layers (that is, correction by using the multi-bracket is continued). As described above, the correction device 100 can also be used as a rescue system of the multi-bracket. That is, orthodontic treatment providing a synergistic effect obtained by combining the advantage obtained by the multi-bracket with the advantage obtained by the correction device 100 is also possible. The structure in which the grip member includes two layers, i.e., the lower layer and the upper layer is effective, in particular, in the case of crowding in the oral cavity of a patient similarly to the case where a multi-bracket is used.

Figure 15:
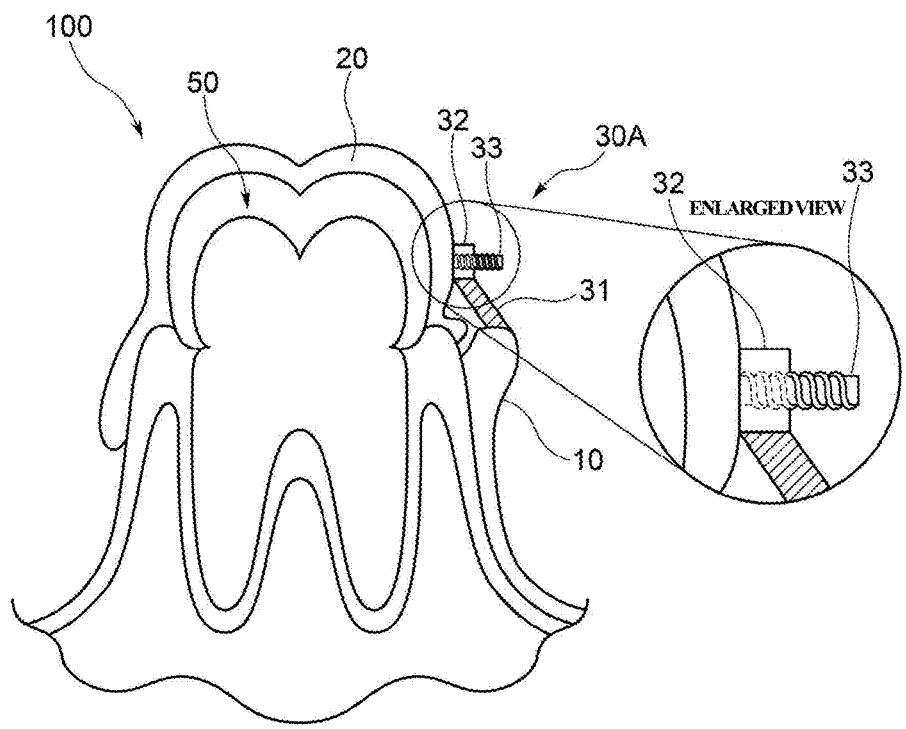
FIG. 15 is a cross-sectional view illustrating an example structure of a variation of a force applying member provided to connect a first piece and a second piece of the correction device according to the embodiment of the present invention.

FIG. 15 illustrates an example structure of a variation of the force applying member 30 provided to connect the first piece 20 to the second piece 10 of the correction device 100 according to the embodiment of the present invention.

As illustrated in FIG. 15, the correction device 100 according to the present embodiment uses a screw 30A serving as a force applying member. The screw 30A includes for example, a main screw part 33 made of a known set screw, a screw receiving part 32 through which the main screw part 33 can pass, and a support member 31 placed on the second piece 10 and supporting the screw receiving part 32. When the main screw part 33 is turned, the main screw part 33 advances toward the screw receiving part 32 to press the first piece 20, or when the main screw part 33 is reversely turned, the screw part 33 moves away from the screw receiving part 32. In this way, the correction target tooth 50 can be moved in the buccal side direction or the lingual side direction. Thus, by using the screw 30A having such a special structure, a force applying member 30 which reduces discomfort of a patient can be realized even in a space of the narrow oral cavity.

Figure 16:
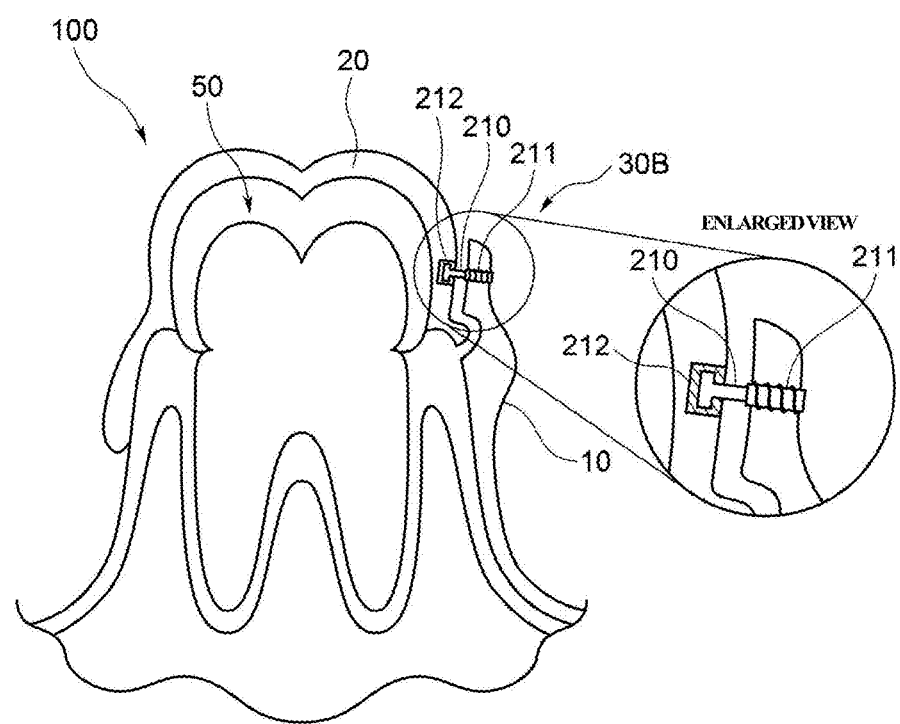
FIG. 16 is a cross-sectional view illustrating an example structure of a variation of the force applying member provided to connect the first piece and the second piece of the correction device according to the embodiment of the present invention.

FIG. 16 illustrates an example structure of a variation of the force applying member 30 provided to connect the first piece 20 to the second piece 10 of the correction device 100 according to the embodiment of the present invention.

As illustrated in FIG. 16, the correction device 100 according to the present embodiment uses a screw 30B serving as a force applying member. The screw 30B includes for example, a main screw part 211 made of a known set screw, a relay member 210 formed continuously with the main screw part 211 and having no screw function, and a screw receiving part 212 which is formed to match the shape of the relay member 210 in a female-male relationship. The main screw part 33 is turned so that the main screw part 33 advances toward the screw receiving part 32, thereby pressing the screw receiving part 212 via the relay member 210 to move the correction target tooth 50 in the buccal side direction or the lingual side direction. At this time, the relay member 210 itself presses the screw receiving part 212 while the relay member 210 is idly turned. Alternatively, the main screw part 33 is reversely turned so that the main screw part 33 advances in a direction away from the screw receiving part 32, and the screw receiving part 212 is pulled via the relay member 210 toward the main screw part 33. In this way, the correction target tooth 50 can be moved in the buccal side direction or the lingual side direction. Thus, by using the screw 30B having such a special structure, a force applying member 30 which reduces discomfort of a patient can be realized even in a space of the narrow oral cavity.

Figure 17:
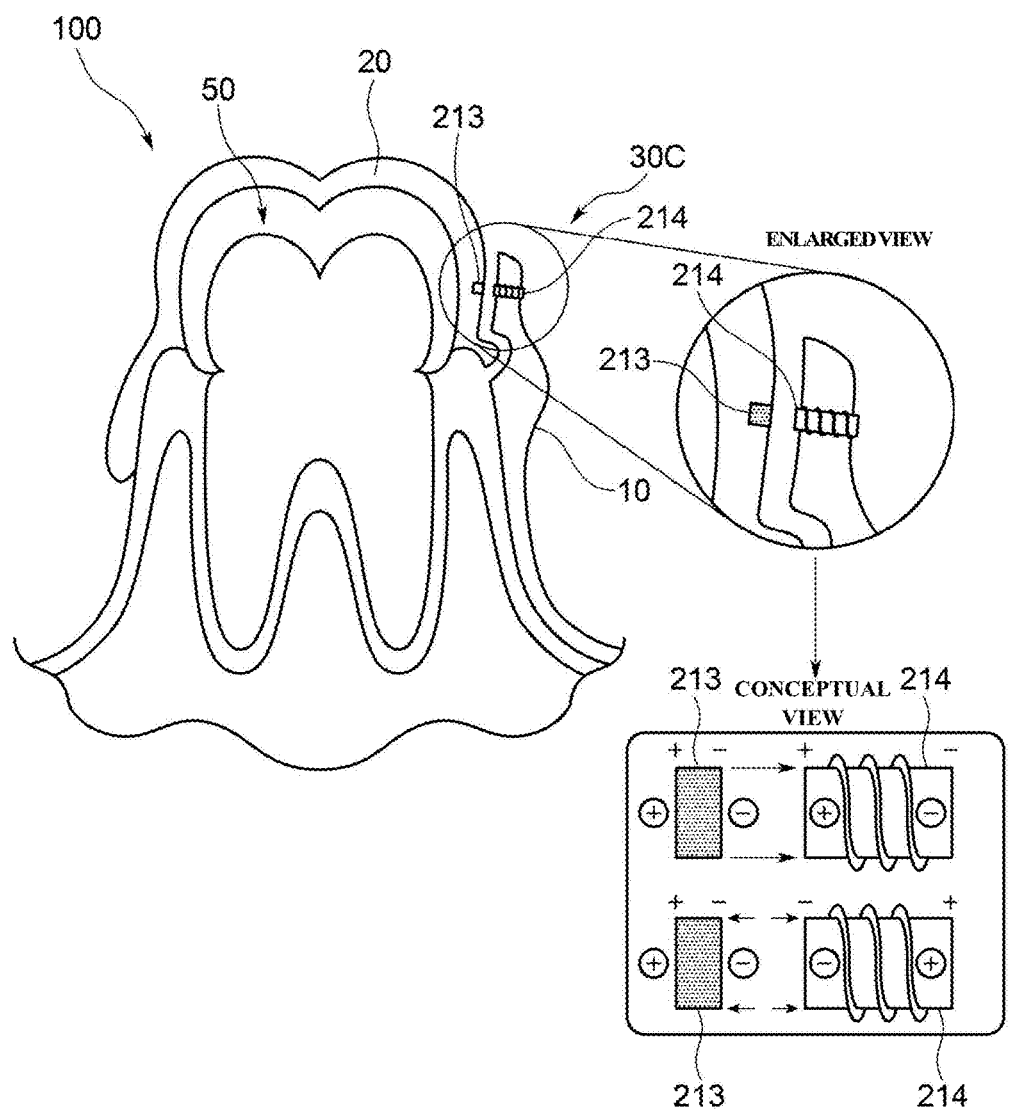
FIG. 17 is a cross-sectional view illustrating an example structure of a variation of the force applying member provided to connect the first piece and the second piece of the correction device according to the embodiment of the present invention.

FIG. 17 illustrates an example structure of a variation of the force applying member 30 provided to connect the first piece 20 with the second piece 10 of the correction device 100 according to the embodiment of the present invention.

As illustrated in FIG. 17, the correction device 100 according to the present embodiment uses a screw 30C serving as a force applying member. The screw 30C includes for example, a first magnet part 214 having a known set screw form, and a second magnet part 213 provided at a position facing the first magnet part 214. The first magnet part 214 is implanted in the second piece 10, and the second magnet part 213 is implanted in the first piece 20. The first magnet part 214 having the set screw shape is turned to move the first magnet part 214 in a direction toward the second magnet 213 or in a direction away from the second magnet 213. At this time, the positive magnetic poles and the negative magnetic poles of the first magnet part 214 and the second magnet part 213 are arranged as illustrated in for example, in a conceptual view of the figure. In this way, the attracting force or repelling force of the magnets can move the correction target tooth 50 in the buccal side direction or the lingual side direction. Thus, by using the screw 30C having such a special structure, a force applying member 30 which reduces discomfort of a patient can be realized even in a space of the narrow oral cavity. A configuration in which the second magnet part 213 is provided so as to be inclined from the vertical direction to the buccal direction or the lingual direction, and the first magnet part 214 is implanted in the second piece 10 at a position facing the second magnet part 213 is effective to move the correction target tooth 50 in the buccal side direction or the lingual side direction while obliquely moving the correction target tooth 50 as described in FIG. 14. The support member 31 illustrated in FIG. 15 is applicable to the variations illustrated in FIG. 16 or FIG. 17 with appropriate modification of the design of the support member 31 illustrated in FIG. 15.

In the embodiment described above, the transparent resin from which the grip member is made may contain carbon. With this configuration, the gripping forces of the first piece 20 and the second piece 10 can be enhanced, so that more stable anchorage is ensured, and movement of the correction target tooth in a desired direction by the force applying member can be further ensured. When the grip member made of a transparent resin is used as an aligner, carbon is partially used so that a portion which is preferably flexible and a portion which is preferably non-flexible are formed to have the same resin thickness. In this way, it is also possible to handle movement of a long tooth row depending on the condition of the tooth row of a patient.

In the embodiment described above, a configuration including the above-described first piece 20, the above-described second piece 10, and the force applying member 30 placed to connect the first piece 20 to the second piece 10 has been described. However, for example, a configuration in which the first piece 20 is not connected to the second piece 10, that is, a configuration in which the first piece 20 gripping, for example, the correction target tooth is independent of the second piece can also move the correction target tooth gripped by the first piece 20 in a desired direction by using, for example, the known set screw described above as a force applying member and implanted in a desirable position of the first piece 20 while the anchorage of the second piece 10 is ensured. As described above, correction is performed with the screw being directly in contact with the correction target tooth. Therefore, a flexible material such as a cap made of, for example a resin or rubber is preferably attached to the distal end of the screw. This is to protect the correction target tooth.

The set screw used as an example in the above-described embodiment is applicable not only in the correction device according to the present embodiment of the present invention but also other orthodontic correction devices such as expansion screws used, for example, for expansion plates.

Cases using the correction devices described in the above embodiment will be described below.

FIGS. 18(*a*)-18(*d*), FIGS. 19(*a*)-19(*d*), and FIGS. 20(*a*)-20(*d*) are pictures showing cases 1-3 in each of which the correction device according to an embodiment of the present invention is used. In each of the pictures of cases 1-3, a broken line is shown so as to clearly indicate that the first piece and the second piece of the correction device are separated.

FIGS. 18(*a*)-18(*d*) show case 1 in which the correction device is used for the upper jaw of a patient. Specifically, FIG. 18(*a*) shows a state before treatment in which the correction device is not placed. In this state, it can be seen that between the third tooth and the fifth tooth from the back on the right in the plane of the paper, there is no space for the fourth tooth which is in the course of the eruption. In such a state, exodontics is often selected to ensure a space for the eruption. However, in case 1, placing the device to cause distal movement of the three teeth from the back was selected. As illustrated in FIG. 18(*b*), the correction device was placed and the treatment was started. Specifically, a grip member formed to fit the shape of the oral cavity on the upper jaw side of the patient was cut into a piece for gripping the three teeth from the back on the right in the figure and a piece for gripping the other entire teeth. A screw was provided as a force applying member to connect the pieces. Here, the screw is turned little by little for days. As a result, in FIG. 18(*c*) which shows a state in the course of the treatment and in which the correction device is placed, it can be seen that the three teeth from the back on the right in the plane of the paper gradually moved in a mesial direction (in a back direction), and finally, as shown in FIG. 18(*d*), a space for the eruption of the fourth tooth is ensured.

FIGS. 19(*a*)-19(*d*) show case 2 using the correction device for the lower jaw of the patient. Specifically, in FIG. 19(*a*) which shows a state before treatment and in which no correction device is placed, it can be seen that the width between the left tooth row and the right tooth row is narrow, and thus no sufficient space is provided for four front teeth on the upper side in the figure and thus, the four front teeth are misaligned. The correction device was placed as illustrated in FIG. 19(*b*) and the correction was started. Specifically, a grip member formed to fit the inner shape of the oral cavity on the lower jaw side of a patient was cut at the upper center in the plane of the paper into pieces which grip neither the four front teeth nor teeth on both side of the four front teeth, but each grip the remaining teeth which are located symmetrically on the right and the left. A screw as a force applying member was provided to connect the pieces. The screw was provided on portions extending from the pieces gripping the remaining teeth located symmetrically on the right and the left to the lingual side of the front teeth, and horizontal movement of the left tooth row and the right tooth row was uniformly caused to increase the width therebetween. Here, when the screw was turned little by little for days, as FIG. 19(c) shows a state after the correction and in which device is placed, the remaining teeth located symmetrically on the right and the left in the figure moved to the buccal side. As a result, it can be seen that the space for the four front teeth was ensured, and the four teeth were aligned and corrected (see also FIG. 19(d) which shows a state after the treatment and in which no correction device is placed).

Figure 20A:
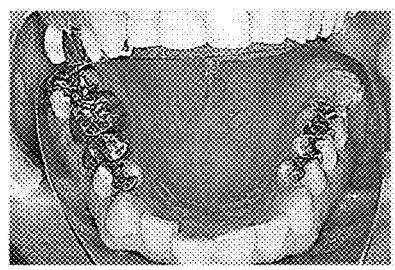
FIGS. 20(a)-20(d) are views illustrating case 3 in which a correction device according to an embodiment of the present invention.
Figure 20B:
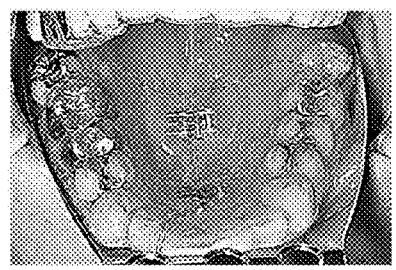
Figure 20C:
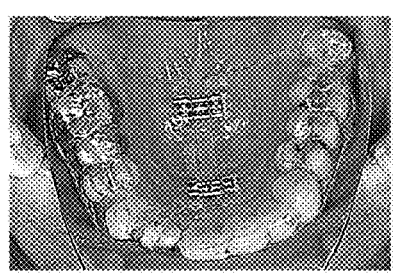
Figure 20D:
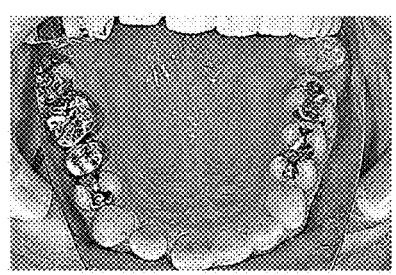

FIGS. 20(a)-20(d) show case 3 in which the correction device is used for the upper jaw of a patient. Specifically, FIG. 20(a) shows a state which is before treatment and in which no correction device is placed. In this state, it can be seen that the second to sixth teeth from the back located on the left in the figure are displaced to the lingual side. As illustrated in FIG. 20(b), the correction device was placed, and treatment was started. Specifically, a grip member formed to fit to the inner shape of the oral cavity on the upper jaw of a patient was cut into pieces at a position near the sixth tooth from the back located on the left in the figure, and a palate portion was cut at its center to be symmetric on the right and the left in the plane of the paper. A screw as a force applying member was provided to connect the pieces to each other. Here, two screws were provided along the cut line. The two screws ere termed little by little for days. From FIG. 20(c) which shows a state after the treatment and in which the correction device is placed, it can be seen that the second to sixth teeth located on the left in the figure moved to the buccal side (see also FIG. 20(d) which shows a state after the treatment and in which no is placed).

As described above, as illustrated cases 1-3 of FIGS. 18(a)-18(d), FIGS. 19(a)-19(d), and FIGS. 20(a)-20(d), when the correction device of the present invention is used, a correction target tooth gripped by the grip member can be reliably moved in a desired direction by the force applying member while at least one of the first piece or the second piece which form the grip member and independent of each other is used as a strong anchorage. When the device is divided at its center into left and right pieces to obtain the first piece and the second piece having a same size, the left and right tooth rows can be uniformly and reliably moved by opposite force from the force applying member. In this way, the correction device can easily and reliably move the correction target tooth in a desired direction while ensuring a satisfactory anchorage. So that highly predictable treatment can be realized.

INDUSTRIAL APPLICABILITY

The present invention is useful in the field of orthodontics.

What is claimed is:

1. A correction device for moving a correction target tooth of a patient in a desirable direction, the correction device comprising:
a grip member formed to fit to an inner shape of an oral cavity of the patient so as to grip and cover a tooth row of the patient, gum parts, and alveolar bone parts on both of a buccal side and a lingual side of the tooth row, wherein
the grip member includes
a first piece, and
a second piece independent of the first piece,
a force applying member provided to connect the first piece to the second piece and configured to move the correction target tooth in the desired direction is further provided, and
the force applying member is formed to fit to the tooth row, and
the length direction of the force applying member is a distal or mesial direction, a lingual side or buccal side direction, or an upward or downward direction with respect to the tooth row.

2. The correction device of claim 1, wherein
when the correction device is used on an upper jaw side, the grip member further includes a palate portion continuous with a portion covering the alveolar bone part on a lingual side of the tooth row and formed to fit to a shape of a palate.

3. The correction device of claim 1, wherein
the first piece grips the correction target tooth to cover an area extending from a crown part to a periphery of a cervical part of a tooth row of the patient, and the second piece covers an area extending from a crown part to a periphery of a cervical part of a tooth row of the patient.

4. The correction device of claim 3, wherein a skeletal anchor is implanted in the second piece.

5. The correction device of claim 1, wherein
the first piece grips the correction target tooth to cover an area extending from a crown part to a periphery of a cervical part of a tooth row of a patient,
the second piece grips a correction target tooth, which is different from the correction target tooth gripped by the first piece, to cover an area extending from a crown part to a periphery of a cervical part of a tooth row of the patient, and
when the correction device is used for a lower jaw, the first piece and the second piece extend to positions close to front teeth, and the force applying member is positioned near the front teeth.

6. The correction device of claim 2, wherein
the first piece grips the correction target tooth to cover an area extending from a crown part to a periphery of a cervical part of a tooth row of a patient,
the second piece grips a correction target tooth, which is different from the correction target tooth gripped by the first piece, to cover an area extending from a crown part to a periphery of a cervical part of a tooth row of the patient, and
when the correction device is used for an upper jaw, the force applying member is provided on the palate portion.

7. The correction device of claim 1, wherein
the first piece grips the correction target tooth to cover an area extending from the crown part to the periphery of the cervical part of a tooth row of the patient, and
a skeletal anchor is implanted in the second piece.

8. The correction device of claim 1, wherein
the desired direction is a distal or mesial direction, a lingual side or buccal side direction, or an upward or downward direction with respect to the tooth row, and
a skeletal anchor is implanted in the second piece.

9. A correction device for moving a correction target tooth of a patient in a desirable direction, the correction device comprising:
a grip member formed to fit to an inner shape of an oral cavity of the patient so as to grip and cover a tooth row of the patient, gum parts, and alveolar bone parts on both of a buccal side and a lingual side of the tooth row, wherein the grip member includes
a first piece, and
a second piece independent of the first piece,
a force applying member provided to connect the first piece to the second piece and configured to move the correction target tooth in the desired direction is further provided,
the first piece grips the correction target tooth to cover an area extending from a crown part to a periphery of a cervical part of a tooth row of a patient,
the second piece grips a correction target tooth, which is different from the correction target tooth gripped by the first piece, to cover an area extending from a crown part to a periphery of a cervical part of a tooth row of the patient, and
when the correction device is used for an upper jaw, the grip member further includes a palate portion continuous with a portion covering the alveolar bone part on a lingual side of the tooth row and formed to fit to a shape of a palate, the force applying member is provided on the palate portion,
a third piece forming the grip member, formed independently of and near the first piece and the second piece, and covering an area extending from the crown part to the periphery of the cervical part of a tooth row of the patient; and
a fixing member connected to the force applying member and extending from the force applying member to the third piece, and
wherein the third piece is formed to surround a circumference excluding each edge portion of the first piece and the second piece.

10. A correction device for moving a correction target tooth of a patient in a desirable direction, the correction device comprising:
a grip member formed to fit to an inner shape of an oral cavity of the patient so as to grip and cover a tooth row of the patient, gum parts, and alveolar bone parts on both of a buccal side and a lingual side of the tooth row, wherein
the grip member includes
a first piece, and
a second piece independent of the first piece,
a force applying member provided to connect the first piece to the second piece and configured to move the correction target tooth in the desired direction is further provided, wherein
the force applying member is formed to fit to the tooth row, and
the length direction of the force applying member is a lingual side or buccal side direction with respect to the tooth row, and wherein
when there is a correction target tooth to be obliquely moved in the lingual side or buccal side direction, a portion of the grip member covering the crown part of the correction target tooth to be obliquely moved is removed on the buccal side or the lingual side.

11. The correction device of claim 1, wherein
the force applying member is a wire, a screw, a spring, an orthodontic rubber, or a magnet.

12. The correction device of claim 11, wherein
the screw, the spring, the orthodontic rubber, or the magnet may be provided to extend over the first piece and the second piece in a direction corresponding to the desired direction.

13. The correction device of claim 12, wherein
the first piece and the second piece each has a portion into which a screw, spring, orthodontic rubber, or a magnet is incorporated, and the portion is formed as a thick part.

14. The correction device of claim 1, wherein the grip member is made of a transparent resin.

15. The correction device of claim 14, wherein
the grip member preferably has a portion having a two-layer structure, and
the portion having the two-layer structure includes a lower layer which is a membrane sheet made of silicon and an upper layer made of the transparent resin.

16. The correction device of claim 14, wherein the transparent resin contains carbon.

17. The correction device of claim 1, wherein the grip member covers a region including the tooth row, the gum parts, and highest contour portions of the alveolar bone part on the buccal side of the tooth row.

18. The correction device of claim 1, wherein the grip member is configured to grip the entire tooth row of a patient.

19. A correction device for moving a correction target tooth of a patient in a desirable direction, the correction device comprising:
a grip member formed to fit to an inner shape of an oral cavity of the patient so as to grip and cover a tooth row of the patient, gum parts, and alveolar bone parts on both of a buccal side and a lingual side of the tooth row, wherein
the grip member includes
a first piece, and
a second piece independent of the first piece, and
a force applying member provided to connect the first piece to the second piece and configured to move the correction target tooth in the desired direction is further provided, wherein
the first piece is used for the upper jaw, and covers an area extending from the crown part to the periphery of the cervical part of the entire tooth row of the upper jaw of the patient,
the second piece is used for the lower jaw, and covers an area extending from the crown part to the periphery of the cervical part of the entire tooth row of the lower jaw of the patient,
the force applying member is an intermaxillary rubber, and
a skeletal anchor may be implanted in both or one of the first piece and the second piece.

* * * * *